US006504005B1

(12) United States Patent
Fridkin et al.

(10) Patent No.: US 6,504,005 B1
(45) Date of Patent: Jan. 7, 2003

(54) LONG-ACTING DRUGS AND PHARMACEUTICAL COMPOSITIONS COMPRISING THEM

(75) Inventors: Matityahu Fridkin, Rehovot (IL); Yoram Shechter, Rehovot (IL); Eytan Gershonov, Hod Hasharon (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/242,026

(22) PCT Filed: Aug. 5, 1997

(86) PCT No.: PCT/IL97/00265

§ 371 (c)(1),
(2), (4) Date: Feb. 5, 1999

(87) PCT Pub. No.: WO98/05361

PCT Pub. Date: Feb. 12, 1998

(30) Foreign Application Priority Data

Aug. 7, 1996 (IL) .................................................. 119029

(51) Int. Cl.[7] .............................................. A61K 38/28
(52) U.S. Cl. .............................. 530/303; 514/1; 514/2; 514/3; 530/336; 530/337; 530/399; 530/402
(58) Field of Search .............................. 514/12, 1, 2, 3; 530/336, 337, 303, 399, 402

(56) References Cited

U.S. PATENT DOCUMENTS

| 5,242,927 A | 9/1993 | Baker et al. | |
| 5,631,222 A | 5/1997 | Shibata et al. | 514/9 |
| 5,846,934 A | * 12/1998 | Bass et al. | 514/11 |
| 6,057,297 A | * 5/2000 | Politi | 514/19 |
| 6,313,094 B1 | * 11/2001 | Mimoto | 514/18 |

FOREIGN PATENT DOCUMENTS

| WO | WO 88/02756 | 4/1988 |
| WO | WO 95/21622 | 8/1995 |
| WO | WO 96/12505 | 5/1996 |
| WO | WO 96/23794 | 8/1996 |
| WO | WO 96/30332 | 10/1996 |

OTHER PUBLICATIONS

Ken Inouye et al. "Insulin Synthesis with $N^{\alpha B1}$FMOC–DOI as Intermediate" Peptide Chemistry, N. Izumiya Ed. Protein Research Foundation, Osaka pp. 193–198, 1984.*
JP 54145206A Nov. 13, 1979 Abst. only "Blood Sugar Lowering Drum for Oral Administration", 1979.*
Patent abstract of Japanese application No. 94-141007.
Patent abstract of Japanese application 63–06097.
Leyer, Sigmar et al., "The role of the C–terminus of the insulin B–chain in modulating structural and functional properties of the hormone.", Inte. Journ. of Pep. & Prot. Res., vol. 46, pp. 397–407 (1995).

Bodansky, Miklos et al., "Derivatives of S–9–fluorenylmethyl–L–cysteine.", Int. J. Pep. Protein Res., vol. 20, pp. 434–437 (1982).
Burch, Ronald et al., "N–(Fluorenyl–9–methoxycarbonyl) amino acids, a class of anti–inflammatory agents with a different mechanism of action.", Proc. Natl. Acad. Sci., vol. 88, pp. 355–359 (1991).
Campbell, Keith et al., "Insulin lispro:its role in the treatment of diabetes mellitus," Annals of Pharmacotherapy, vol. 30, pp. 12631271 (1996).
Gertler, A. et al., "Binding sites of human growth hormone and ovine and bovine prolactins in the mammary gland and the liver of lactating dairy cow.", Mole. Cell. Endo., vol. 34, pp. 51–57 (1984).
Kaarsholm, Niels et al., "The high resolution solution structure of the insulin monomer determined by NMR.", Receptor, vol. 5, pp. 1–8 (1995).
Meyerovitch, Joseph et al., "Oral administration of vanadate normalized blood glucose levels in streptozotocin–treated rats,", J. Biol. Chem., vol. 262, No. 14, pp. 6658–6662 (1987).
Meyerovitch, Joseph et al., "A family of polypeptide substrates and inhibitors of insulin receptor kinase.", Biochemistry, vol. 29, pp. 3654–3660 (1990).
Moody, A.J. et al., "A simple free fat cell bioassay for insulin,", Horm. Metab. Res., vol. 6, pp. 12–16 (1974).
Pederson, Raymond et al., "Long–term effects of Vanadyl treatment on streptozocin–induced diabetes in rats." Diabetes, vol. 38, pp. 1390–1395 (1989).
Rodbell, Martin, "Metabolism of isolated fat cells.", J. Biol. Chem., vol. 239, No. 2, pp. 375–380 (1964).
Schechter, Yoram, "Evaluation of adenosine or related nucleosides as physiological regulators of lipolysis in adipose tissue.", Endocrinology, vol. 110, No. 5, pp. 1579–1583 (1982).
Schechter, Yoram et al., "Effect of depletion of phosphate and bicarbonate ions on insulin action in rat adipocytes.", J. Biol. Chem., vol. 261, No. 32, pp. 14945–14950 (1986).

* cited by examiner

Primary Examiner—Christopher S. F. Low
Assistant Examiner—David Lukton
(74) Attorney, Agent, or Firm—Browdy and Neimark, PLLC

(57) ABSTRACT

Disclosed are conjugates of a polypeptide or oligopeptide with a low molecular weight lipophilic compound, the peptide and lipophilic group being covalently linked to one another either directly or via a connecting element, with the exception of (a) conjugates in which the peptide component consists of hirudin or peptide structurally derived from hirudin or a peptide derivative with hirudin-like properties, and (b) conjugates whose peptide component has been hydrophobically modified during their biosynthesis.

39 Claims, 7 Drawing Sheets

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence -continued

```
<220> FEATURE:
<223> OTHER INFORMATION: Description of Artificial Sequence: Repeating
      unit of poly-mer

<400> SEQUENCE: 1

Glu Glu Glu Glu Tyr
  1               5
```

LONG-ACTING DRUGS AND PHARMACEUTICAL COMPOSITIONS COMPRISING THEM

FIELD OF THE INVENTION

The present invention relates to novel long-acting prodrugs capable of undergoing chemical transformation in the body from an inactive into a bioactive form, said prodrugs bearing functional groups sensitive to mild basic conditions, more particularly fluorenylmethoxycarbonyl (Fmoc)- and fluorenylmethyl (Fm)-substituted prodrugs, and to pharmaceutical compositions comprising them.

BACKGROUND OF THE INVENTION

Therapeutical drugs currently being used both in human therapy and veterinary can be classified according to various criteria. For example, drugs may be categorized as molecules having a proteinaceous-peptidic, i.e. composed of amino acid building units, or non-peptidic character, or by a criterion unrelated to the structure such as drugs absorbed orally or administered by other modes, i.e. injection, intranasal or topical, in order to reach the blood circulation.

Orally absorbed compounds are, in general, low molecular weight, rather stable, lipophilic ("oily") and of a non-peptidic nature. Virtually all peptidic and protein drugs, due to their intrinsic hydrophilic (non-lipophilic) and polar features and metabolical instability, do not obey these criteria and must be administered mostly by injection. Further, as these molecules are rapidly degraded in the body by diverse mechanisms, notably proteolysis, they are usually short-living species.

Non-peptidic drugs are very often sufficiently hydrophobic and can reach the blood circulation through the gastrointestinal pathway. Due to their relative chemical stability, the non-peptidic drugs are usually long-living species.

Protein and peptide drugs have major and numerous clinical applications. e.g. insulin in the treatment of diabetes, gonadotropin-releasing hormone (GnRH) analogs in the therapy of prostate cancer, calcitonin in the treatment of bone-related disorders. The potential for this most important family of molecules is vast, but has as yet been only partially, if not marginally, explored. This, to large extent, is due to their short life in the body and inconvenience of the mode of administration. Non-peptidic drugs, such as antibiotics, although relatively long-lived, have to be administered several times a day over a period of a week, or longer, to maintain the desired continuous circulating levels.

Oral absorption of drugs is a highly desirable goal in the treatment of human diseases, particularly in prolonged therapeutical treatments. Structural alteration of drugs may result in the augmentation of oral and topical absorption, biostability and, eventually, bioavailability. Major efforts are currently being directed toward these goals. Most approaches include drug modification in such way that its native architecture, i.e. bioactive structure, is preserved. This native structure is the one recognized specifically by the drug's target and is a prerequisite feature of the drug's potency. Unfortunately, however, in many cases, the native structure is also recognized by the 'clearing machinery system', which is capable of binding the drug, degrading or metabolizing it and thus accelerates its disposal. Thus, stabilization of the bioactive structure is often attempted concomitantly with the desire to enhance metabolic stability. Methods such as encapsulation, decreased solubility and chemical modification have been employed to achieve this goal.

It would be highly desirable to prolong the half-life of virtually many, if not all peptidic as well as non-peptidic drugs existing on the market or to be developed in the future, including antibiotics, antiviral, antihypertensive, antiinflammatory, analgesic, anticholesterolemia, anticarcinogenic, antidiabetic, growth-promoting, and other drugs. Prodrugs related to native drugs that are toxic above certain threshold concentrations might be particularly beneficial.

SUMMARY OF THE INVENTION

It is therefore an object of the present invention to provide novel prodrugs characterized by their high sensitivity to mild basic conditions and their capability of undergoing transformation from an inactive into a bioactive form under physiological conditions in the body.

It is another object of the present invention to provide prodrugs derived from drugs having free amino, carboxyl, hydroxyl and/or mercapto groups, said prodrugs being essentially non-active biologically but being capable of spontaneous and slow conversion to the original active drug molecule in the body, following administration.

It is still another object of the present invention to provide prodrugs that present higher metabolic stability and augmented bioavailability.

It is a further object of the present invention to provide prodrugs that represent alternative possibilities for drug administration, e.g. oral and transdermal, and are further capable of penetrating through physiological barriers, e.g. blood-brain-barrier.

It is still a further object of the present invention to provide prodrugs that permit specific drug targetting to inflicted locations in the body.

The present invention thus relates to novel prodrugs derivatized from a drug in which one or more groups of said drug molecule selected from the group comprising free amino, carboxyl, hydroxyl and/or mercapto, are substituted by functional groups sensitive to bases and removable under mild basic. e.g. physiological, conditions.

The new concept of the invention for slow-releasing drugs includes their derivatization into novel, generally more hydrophobic, drug derivatives. In this approach it is preferred to lose, rather than to preserve, the native conformation, the biological potency and the recognition identity of the drug by the degradative systems. An advantage of this approach, however, resides in the fact that the thus modified derivative can slowly and spontaneously hydrolyze back to the native active drug under the in vivo conditions.

In a particular embodiment, the prodrugs of the invention are of the formula:

$$X—Y$$

wherein

Y is a moiety of a drug bearing at least one functional group selected from free amino, carboxyl, hydroxyl and/or mercapto, and X is a radical selected from radicals of the formulas (i) to (iv):

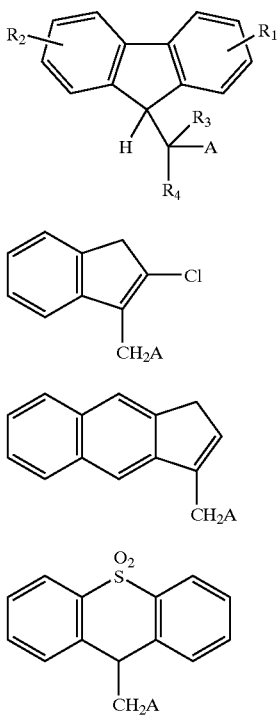

wherein $R_1$ and $R_2$, the same or different, are each hydrogen, alkyl, alkoxy, alkoxyalkyl, aryl, alkaryl, aralkyl, halogen, nitro, sulfo, amino, ammonium, carboxyl, $PO_3H_2$, or $OPO_3H_2$; $R_3$ and $R_4$, the same or different, are each hydrogen, alkyl or aryl; and A is a covalent bond when the radical is linked to a carboxyl or mercapto group of the drug Y, or A is OCO— when the radical is linked to an amino or hydroxyl group of Y.

According to the present invention, Y is a moiety of any drug for human and veterinary use bearing at least one functional group selected from free amino, carboxyl, hydroxyl and/or mercapto, such as, but not being limited to, antidiabetic drugs, e.g. insulin; growth promoters, e.g. human growth hormone, bovine growth hormone; antibiotics such as aminoglycosides, e.g. gentamicin, neomycin and streptomycin, β-lactams, such as penicillins, e.g. amoxicillin, ampicillin, piperacillin, and cephalosporins, e.g. cefaclor, cefminox and cephalexin, macrolides, e.g. carbomycin and erythromycin, and polypeptidic antibiotics. e.g. bacitracin, gramicidins and polymyxins; synthetic antibacterials, e.g. trimethoprim, piromidic acid, and sulfamethazine; analgesic and anti-inflammatory drugs. e.g. acetaminophen, aspirin, ibufenac, indomethacin; antiallergic and antiasthmatic drugs, e.g. amlexanox and cromolyn; antihypercholesterolemic drugs, e.g. clofibric acid, oxiniacic acid and triparanol; β-adrenergic blockers and antihypertensive drugs, e.g. bupranolol, captopril, indenolol, propranolol and 4-aminobutanoic acid; antineoplastic drugs, e.g. daunorubicin, azacitidine, 6-mercaptopurine, interferons, interleukin-2, methotrexate, taxol and vinblastine; antiviral drugs, e.g. acyclovir, ganciclovir, amantadine, interferons, AZT and ribavirin, etc. The term drug according to the invention is intended to encompass also pheromones.

The terms "alkyl", "alkoxy", "alkoxyalkyl", "aryl", "alkaryl" and "aralkyl" in the definitions of $R_1$, $R_2$, $R_3$ and $R_4$ herein are used to denote alkyl radicals of 1–8, preferably 1–4 carbon atoms, e.g. methyl, ethyl, propyl, isopropyl and butyl, and aryl radicals of 6–10 carbon atoms, e.g. phenyl and naphthyl. The term "halogen" includes bromo, fluoro, chloro and iodo.

In a preferred embodiment of the invention, the functional group is the radical (i), wherein $R_1$, $R_2$, $R_3$ and $R_4$ are hydrogen and A is OCO—, i.e. the well-known 9-fluorenylmethoxycarbonyl (Fmoc) radical widely used in peptide synthesis for the temporary reversible protection of amino groups (for review, see L. A. Carpino, Acc. Chem. Res. (1987) 20,401–407). The Fmoc group is particularly suitable for peptide synthesis due to favorable synthetic manipulation for its introduction and removal, and preferential stability as a prerequisite for peptide synthesis and convenient purification. Furthermore, the related 9-fluorenylmethyl (Fm) group is also applicable for reversible masking of carboxylic functions, e.g. of amino acids. The resulting 9-fluorenylmethyl esters (Fm-esters) generate the parent free carboxylic functions following a β-elimination reaction pathway upon mild basic treatment, and thus can be similarly employed for reversible masking of carboxylic functions of drugs. The Fmoc-group is of further potential similar use in the reversible protection of hydroxyl groups of tyrosine, serine and threonine.

The halogenated Fmoc radicals (i) wherein at least one of $R_1$ and $R_2$ is halogen in the 2 or 7 position, preferably Cl or Br, the 2-chloro-1-indenylmethoxycarbonyl (CLIMOC) radical (ii), the 1-benzo[f]indenylmethoxycarbonyl urethane (BIMOC) radical (iii), the urethane sulfone radical (iv) and corresponding radicals (i) to (iv) wherein A is a covalent bond, can be used similarly to Fmoc and Fm for substitution of free amino, carboxyl, hydroxyl and mercapto functions of drugs, thus providing a wide range of sensitivity toward removal of such groups under basic, e.g. physiological, conditions. In fact, the above radicals (i) to (iv) belong to a general family of rare chemical entities that undergo hydrolysis at neutral or slightly alkaline pH and mild conditions, and can therefore be used for temporary reversible protection of α- and ε-amino groups, for example in peptide synthesis, and can be removed from the amino function by a β-elimination reaction, under mild basic conditions.

According to the invention the radical (i) to (iv), preferably Fmoc covalently linked to amino and/or hydroxyl moieties, or Fm covalently linked to carboxyl and/or mercapto moieties, undergo hydrolysis (via β-elimination) back to the free amino, hydroxy, mercapto or carboxyl functions, under physiological conditions in the body fluid, namely at pH 7.4 and 37° C.

The prodrugs of the invention may be prepared by reaction of the drug molecule with a suitable reagent comprising a radical (i) to (iv). Several derivatives of 9-fluorenylmethyl (Fm) are available, such as 9-fluorenylmethyl-N-hydroxysuccinimide (Fmoc-OSu), a very specific reagent for amino functions; 9-fluorenylmethoxycarbonyl chloride (Fmoc-Cl) that reacts with, and covalently attaches to, amino and hydroxyl radicals; 9-chloromethylfluorene (Fm-Cl) that reacts with mercapto radicals to yield S-Fm derivatives (Bodanszky and Bednarek, 1982); and 9-fluorenylmethanol (Fm-OH) that reacts with, and esterifies, carboxylic functions.

Functional groups sensitive to basic conditions which can be removed from amino, carboxylic, hydroxylic or mercapto functions following pathways different from β-elimination are also available, but they usually require extensive manipulations not adequate for drug protection. One known exception is the trifluoroacetyl group (TFA) which is rather similar to Fmoc in its easy removal from amino groups, but it is potentially toxic, and thus TFA-dervatized drugs are not recommended for therapeutical purposes. Fmoc-aminoacids, e.g. Fmoc-leucine, on the other hand, were shown to have low index of toxicity in experimental animal models (Burch et al., 1991).

The invention further relates to pharmaceutical compositions comprising a prodrug according to the invention and a pharmaceutically acceptable carrier.

DETAILED DESCRIPTION OF THE INVENTION

Figure 1:
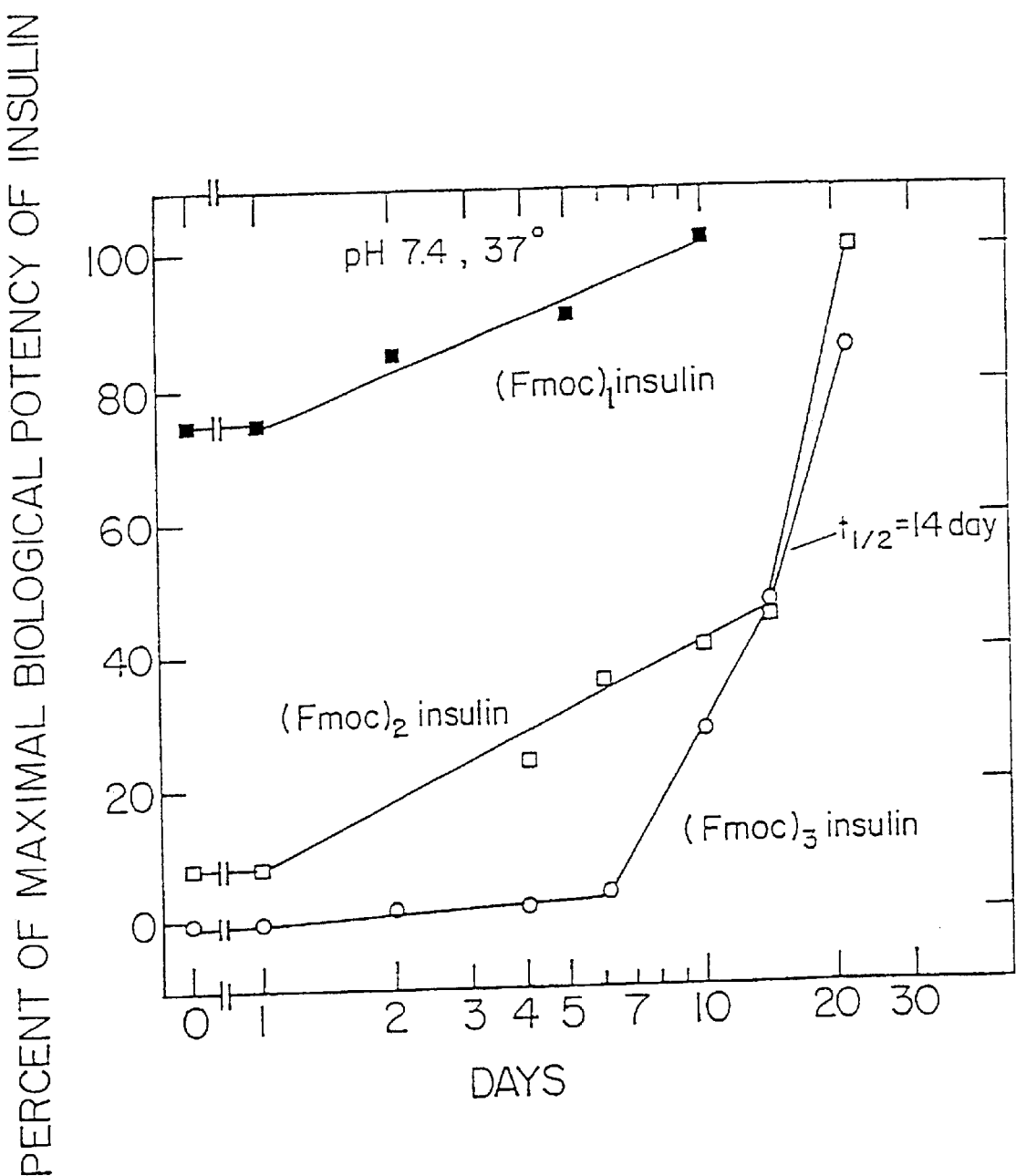
FIG. 1 shows time course of activation (pH 7.4, 37° C.) of either $Lys^{B29}$-N-(Fmoc)$_1$-insulin (closed squares), $Phe^{B1}$, $Lys^{B29}$-N-(Fmoc)$_2$-insulin (open squares) and $Gly^{A1}$, $Phe^{B1}$, $Lys^{B29}$-N-(Fmoc)$_3$-insulin (substituted on all three amino groups, open circles), as determined by cell-free biological assay (phosphorylation of [poly(Glu$_4$Tyr)]SEQ ID NO:1 by enriched preparation of insulin receptor tyrosine kinase).

The present invention relates to prodrugs designed according to a novel concept for developing better routes of drug administration and consequent enhanced drug stability and bioactivity. According to the novel approach of the present invention, it is preferred to lose rather than to preserve the drug's native structure, biological potency and target-recognition capacity but, following application, the thus modified drug will spontaneously and slowly convert back in the body to the original active molecule.

According to the novel concept of the present invention, numerous currently applied drugs can be converted into inactive prodrugs that are long-lived species as they evade general and receptor-mediated degradation in the organism. The prodrugs of the invention are designed to undergo spontaneous regeneration into the original drugs under in vivo physiological conditions and in a homogeneous fashion. The wide spectrum of chemical procedures available for the production of the prodrugs of the invention allow to obtain a rapid or slow rate of reactivation as necessary. Thus given prodrugs may be prepared with physical attributes such as decreased solubility and, therefore, a slower rate of s.c. absorption. In addition, altering the hydrophobicity index of prodrugs, combined with the feature of spontaneous regeneration in blood circulation, permits to convert orally nonabsorptive drugs into gastrointestinal permeable prodrugs.

The prodrugs according to the invention include modified drugs for use in humans and animals as well as modified insect pheromones.

In one aspect of the invention the prodrug is modified insulin. At present, insulin is the predominant drug for diabetes mellitus, a group of syndromes characterized by hyperglycemia, altered metabolism of lipids, carbohydrates and proteins and an increased risk of complications from vascular diseases. Most patients can be classified clinically as having either insulin-dependent (IDDM, Type I) or insulin-independent diabetes mellitus (NIDDM, Type II). In the Western world about 90% of diabetic patients have Type II diabetes and most of the remainder have Type I. About 70% of Type II diabetics in the United States are also obese, a factor that contributes significantly to insulin resistance. In Type I diabetes, there is an extensive and selective loss of pancreatic β-cells and a state of hypoinsulinemia. By contrast there is no significant loss of β-cells from the islets in Type II diabetic patients, in which patients the mean plasma concentration of insulin over a 24-hour period is essentially normal or even elevated because of peripheral resistance to the action of the hormone. Nevertheless, individuals with Type II diabetes are relatively insulin deficient. This is because a normal pancreatic β-cell should be capable of secreting amounts of insulin that are considerably greater than normal when confronted with hyperglycemia, thus allowing an individual to maintain euglycemia in the face of moderate resistance to insulin.

Virtually all forms of diabetes mellitus are due to either a decrease in the circulating concentration of insulin (insulin deficiency) or a decrease in response of peripheral tissues to insulin (insulin resistance), in association with an excess of hormones with actions opposite to those of insulin (glucagon, growth hormone, cortisol, and catecholamines). These hormonal abnormalities lead to alterations in the metabolism of carbohydrates, lipids, ketones and amino acids. The central feature of the syndrome is hyperglycemia.

The half-life of insulin in plasma is about 5–6 min. Degradation of insulin occurs primarily in liver and to a lesser extent in kidney and muscle. About 50% of the insulin that reaches the liver in the portal vein is destroyed and never reaches the general circulation. Insulin is filtered by the renal glomeruli and is reabsorbed by the tubules which also degrade it.

Proteolytic degradation of insulin in the liver is primarily receptor mediated. Following insulin receptor-binding the complex is internalized into small vesicles termed endosomes where degradation is initiated. Some insulin is also delivered to lysosomes for degradation. In hepatocytes about 50% of internalized insulin is degraded.

Insulin is critical for the management of diabetes ketoacidosis, and important in the treatment of hyperglycemic non-ketonic coma, and in the perioperative management of both Type I and Type II diabetic patients. Subcutaneous (s.c.) administration of insulin is the primary treatment for all Type I patients and most Type II diabetic patients who are not adequately controlled by diet and/or oral hypoglycemic agents. In all cases the goal is to normalize, not only blood glucose, but also all other aspects of the unbalanced metabolism resulting from hypoinsulinemia and hyperglycemia.

Long term treatment based primarily on s.c. administration of insulin does not mimic the normal rapid rise and decline of insulin secretion in response to injected nutrients, and possesses preferential peripheral rather than hepatic effects of insulin, but nevertheless considerable success has been achieved with this treatment.

Insulin preparations traditionally utilized for s.c. application are classified according to their duration of action into short, intermediate or long-acting insulins, and according to the species origin. Human insulin is now widely available, and in theory, expected to be less immunogenic than porcine or bovine insulins as the last two differ from human insulin by one and three amino acids, respectively. However, when highly purified, all three insulins have low but measurable capacity to stimulate the immune response. Preparations at neutral pH values are in general stable and permit storage for long periods of time at room temperature. For traditional and therapeutic purposes, doses and concentrations of insulin are expressed in units (U), based on the amount required to induce normoglycemia in fasting rabbits. Homogeneous preparations of insulin contain about 25 U/mg. Almost all commercial preparations of insulin are supplied in solution at a concentration of 100 U/ml.

Short or rapid-acting insulins are soluble preparations of crystalline zinc insulin dissolved in a neutral pH buffer, usually injected 30–45 minutes before meals. These preparations have the most rapid onset of action and the shortest duration.

Under stable metabolic conditions regular insulins are usually administered together with intermediate, or long-acting preparations. Intermediate-acting insulins were designed to be less soluble in aqueous solutions, therefore they dissolve more gradually upon subcutaneous administration and their duration of action is longer. Two preparations most frequently used are NPH Insulin (NPH stands for Neutral Protamine Hagedorn), a suspension of zinc-insulin crystals in phosphate buffer modified by the addition of protamine sulfate, and Lente Insulin, a suspension of insulin in acetate buffer modified by the addition of zinc chloride to minimize solubility of insulin.

Since short-acting insulin is expected to cover a period of 0.4–7 hrs and intermediate-acting insulin may cover a range of 1.5–20 hrs, the correct timing and doses of the combination of the two insulins must take into consideration the variable parameters such as nutritional behavior, night (fasting) hypoglycemia, and morning hyperglycemia, when the activity of the counter-regulatory hormones (to insulin) is increased. If rapid-acting and long or intermediate-acting insulin preparations are coadministered together, a common disadvantage of such combinations is that, upon mixing, some of the rapid-acting insulins can be complexed with excess $Zn^{2+}$ or protamine of the long or intermediate-acting preparation, being thus converted into an intermediate and even long-acting insulin.

Long-acting insulins, such as Ultralente Insulin or extended zinc-insulin or protamine-zinc-insulin suspensions, are insulin preparations in which zinc, or zinc plus protamine, was added in excess in order to achieve insoluble preparations of insulin. They are suspensions of minute particles of zinc-insulin and differ only in the particle size which determines the duration of their action. Unlike regular insulin, Ultralente Insulins have a very slow onset and a prolonged ("flat") peak of action. They advocate to provide a low basal concentration of insulin throughout the day, but their long half-life makes it difficult to determine the optimal dosage and several days of treatment are required before a steady-state concentration can be achieved. Bovine and porcine Ultralente Insulin have more prolonged course of action than does human Ultralente Insulin. It is recommended to initiate the therapy with three times the normal daily dose as a loading dose, followed by once or twice daily injections.

Insulin has three amino and six carboxyl groups available for modification. The insulin derivatives of the invention are substituted at the insulin A and B-chains by one or more of the radicals (i) to (iv) above at one or more of the terminal amino groups of the $Gly^{A1}$ and $Phe^{B1}$ radicals, at the ε-amino groups of the $Lys^{B29}$, at the terminal carboxyl groups of $Asn^{A21}$ and $Thr^{B30}$ and/or at the free carboxyl groups of $Glu^{A4}$, $Glu^{A17}$, $Glu^{B13}$, and $Glu^{B21}$. In addition, the thus substituted carboxyl and/or amino insulin derivatives may be further substituted by one or more of the functional groups (i) to (iv) at one or more of the free hydroxyl groups of the residues $Thr^{A8}$, $Ser^{A9}$, $Ser^{A12}$, $Tyr^{A14}$, $Tyr^{A19}$, $Ser^{B9}$, $Tyr^{B16}$, $Tyr^{B26}$, $Thr^{B27}$ and $Thr^{B30}$. The amino acid residue numbering used in the present specification and claims is that of the human insulin used in the Examples.

In one preferred embodiment of the present invention, the insulin derivatives are substituted by one or more Fmoc moieties at the free terminal amino groups of $Gly^{A1}$ and $Phe^{B1}$, and/or at the ε-amino group of $Lys^{B29}$, thus obtaining insulin derivatives having 1 to 3 Fmoc substituents at the $A^1$, $B^1$ and/or $B^{29}$ positions of the insulin molecule, in particular $Gly^{A1}$-N-(Fmoc)$_1$-, $Phe^{B1}$-N-(Fmoc)$_1$- and $Lys^{B29}$-N-(Fmoc)$_1$-insulin, $Gly^{A1}$, $Phe^{B1}$-N-(Fmoc)$_2$-, $Gly^{A1}$, $Lys^{B29}$-N-(Fmoc)$_2$- and $Phe^{B1}$, $Lys^{B29}$-N-(Fmoc)$_2$-insulin, and $Gly^{A1}$, $Phe^{B1}$, $Lys^{B29}$-N-(Fmoc)$_3$-insulin.

Reaction of insulin with activated Fmoc, for example with 9-fluorenylmethyl-N-hydroxysuccinimide (Fmoc-OSu) yields mono-, di- and tri-N-Fmoc-insulins that can be readily resolved by HPLC procedures and individually obtained in pure form. In order to obtain a di-N-Fmoc-insulin as the sole product, one of the free amino groups is first protected, e.g. with the t-Boc group, the protected insulin derivative is reacted with excess of Fmoc-OSu, and the protecting group is then removed, resulting in the desired di-N-Fmoc-insulin. When administered to diabetic patients, the mono-, di- and tri-N-Fmoc-are converted to native insulin in vivo leading to antidiabetic effects over various, including prolonged, periods of time.

For substitution only of the carboxyl groups of insulin (C-Fm), i.e. in the terminal $Asn^{A21}$ and $Thr^{B30}$ and in the $Glu^{A4}$, $Glu^{A17}$, $Glu^{B13}$ and $Glu^{B21}$ residues, the free amino groups of the insulin molecule are first protected, e.g. with t-Boc groups, and then a reaction of 3 steps is carried out, wherein (1) the free carboxyl groups are converted into active ester groups by reaction, e.g. with o-nitrophenol or N-hydroxy-succinimide; (2) reaction of the activated ester groups with 9-fluorenylmethanol is performed in the presence of imidazole; and (3) the protecting t-Boc groups are removed. An alternative procedure involves a one-step direct esterification of carboxylic groups with N,N'-dicyclohexylcarbodiimide, 9-fluorenylmethanol and 4-dimethylaminopyridine, followed by removal of t-Boc groups.

When Fmoc-insulin derivatives substituted both at the amino and carboxyl groups (N-Fmoc, C-Fm) are desired, the N-Fmoc derivative is first prepared with Fmoc-OSu and the N-Fmoc insulin is then converted to active esters followed by reaction with 9-fluorenylmethanol, as described above.

For preparation of Fm, Fmoc-insulin derivatives substituted at the carboxyl and hydroxyl functions (C-Fm,O-Fmoc), the amino groups are first protected with t-Boc, the C-Fm insulin derivative is prepared as above, followed by reaction with 9-fluorenylmethoxycarbonyl chloride and removal of the protecting N-t-Boc groups.

For preparation of Fm, Fmoc-insulin derivatives substituted at the amino, carboxyl and hydroxyl functions (N, O-Fmoc, C-Fm), the N-Fmoc, C-Fm insulin is prepared as above and is then reacted with 9-fluorenylmethoxycarbonyl chloride.

The modified insulins according to the invention may be prepared from any insulin suitable for human use, such as native, recombinant or mutated human, porcine or bovine insulin. Examples of mutated insulins are the B16-Tyr→His human insulin analog (Kaarsholm and Ludvigsen, 1995) and the $Lys^{B28}Pro^{B29}$ human insulin analog (insulin lispro), in which the naturally occurring amino acid sequence at positions B28 and B29 is reversed. Insulin lispro is equipotent to human insulin and yet absorbed more quickly from subcutaneous injection sites (Campbell et al., 1996). In a preferred embodiment, the insulin is human insulin, either native or recombinant.

The mono-N-Fmoc-insulin derivatives of the present invention have 40–80% of the native insulin biological potency, as determined by the [poly($Glu_4Tyr$)]SEQ ID NO:1 phosphorylating assay. The di- and tri-N-Fmoc-insulin derivatives have 2–9% and <1% the of the native insulin biological potency, respectively, as determined by the [poly(Glu4Tyr)]SEQ ID NO:1 phosphorylating assay. When properly used, in the right proportions, these three prototypes may in principle substitute the traditional mixtures of rapid, intermediate and long-acting insulins currently applied in subcutaneous therapy of diabetes. In the aspect related to insulin, the invention provides pharmaceutical compositions comprising one or more insulin derivatives of the invention and a pharmaceutically acceptable carrier. For long-acting effect, the composition will preferably comprise either the N-$(Fmoc)_3$-insulin or the N-$(Fmoc)_2$-insulin derivative alone or a mixture of both. The pharmaceutical composition may be presented in any suitable form, for example as an oral formulation or for subcutaneous injection.

In another embodiment of this same aspect, the invention relates to a method for treatment of diabetes which comprises administering to a diabetic patient an effective dose of one or more insulin derivatives of the invention. In preferred embodiments, the derivative is either native or recombinant human N-$(Fmoc)_3$-insulin or N-$(Fmoc)_2$-insulin, or a mixture of both, administered at 5–8 day intervals. If necessary, the treatment with the Fmoc-insulin derivative is completed by daily administration of rapid-acting insulin.

For long-term treatment, insulin is mainly administered by subcutaneous injections. Current treatment with long-acting insulins administered subcutaneously suffers from large variations in absorption among individual diabetic patients, due to the fact that the added substances can potentially diffuse away at the site of the subcutaneous injection. The present invention provides insulin derivatives with 'built-in' decreased solubility within the insulin molecule itself. This is expected to eliminate in humans the large variation in subcutaneous absorption and to minimize or even to eliminate interferences upon mixing the analogs as well. The proper mixture of the three N-(Fmoc)-insulin prototypes may cover a prolonged duration of action as it combines the need for rapid-acting insulin, together with the slow-released effects of N-$(Fmoc)_2$ and N-$(Fmoc)_3$-insulin, all of which can be mixed together with no interfering effects.

In another embodiment of this same aspect, the composition of the invention comprises a mixture of mono, di and tri-N-Fmoc-insulin derivatives. N-$(Fmoc)_3$-insulin is basically a long-acting insulin, N-$(Fmoc)_1$-insulins are 40–80% biologically active, as determined by the [poly($Glu_4Tyr$)] SEQ ID NO:1 phosphorylating assay, and exhibit higher solubility in aqueous solutions, and N-$(Fmoc)_2$-insulins are 2–9% biologically active, as determined by the [poly($Glu_4Tyr$)] phosphorylating assay, and are less soluble in aqueous solutions. All three analogs return to fully active insulins upon incubation at 37° C. at physiological pH values. Thus, the proper mixture of the three analogs may give rapid, intermediate and long-acting effect, presently achieved by multiple injections of regular insulin together with preparations containing zinc and protamine.

In other aspects of the present invention, the prodrugs are derived from drugs for human or veterinary use including, but not being limited to, antidiabetic, antiinflammatory, antibacterial, antiviral, antineoplastic and antihypertensive drugs, as well as drugs for treatment of immunological, dermatological and neurological disorders.

The pharmaceutical compositions of the invention comprise the prodrug or a pharmaceutically acceptable salt thereof and a pharmaceutically acceptable carrier. Any suitable route of administration of drugs to humans and animals is envisaged by the invention, for example via conventional injectable, implantable, oral, rectal or topical administration. These preparations can be prepared by conventional methods known to those skilled in the art, for example as described in "Remington's Pharmaceutical Science", A. R. Gennaro, ed., 17th edition, 1985, Mack Publishing Company, Easton, Penn., USA.

The invention will now be illustrated by the following non-limiting Examples.

EXAMPLES

Biological Procedures (i) Preparation of Streptozotocin (STZ)-treated Rats

Male Wistar rats (1 80–200 g) were supplied by the Department of Hormone Research, Weizmann Institute of Science. Diabetes was induced by a single intravenous injection of a freshly prepared solution of streptozotocin (55 mg/kg body weight) in 0.1M citrate buffer (pH 4.5) according to Meyerovitch et al., 1987.

(ii) Enriched preparation of insulin receptor tyrosine kinase was obtained from rat liver membranes as described by Meyerovitch et al., 1990. Briefly, the liver was homogenized in the presence of proteinase inhibitors, solubilized with 1% Triton X-100, and centrifuged. The supernatant was allowed to pass through a wheat-germ agglutinin (WGA)-agarose column (Sigma). Adsorbed insulin receptor portion was eluted with 0.3M N-acetyl-D-glucose amine in 50 mM HEPES buffer, pH 7.4, containing 0.1% Triton X-100, 10% glycerol, and 0.15M NaCl. Biological potencies of insulin and insulin derivatives were evaluated by the assays (iii) and (iv) below.

(iii) Lipogenesis (Incorporation of Labeled Glucose into the Lipids of Intact Adipocytes)

Rat adipocytes were prepared essentially by the method of Rodbell, 1964. The fat pads of male Wistar rats were cut into small pieces with scissors and suspended in 3 ml of KRB buffer containing NaCl, 110 mM; $NaHCO_3$, 25 mM; Kcl, 5 mM; $KH_2PO_4$, 1.2 mM; $CaCl_2$, 1.3 mM; $MgSO_4$, 1.3 mM; and 0.7% BSA (pH 7.4). Digestion was performed with collagenase (1 mg/ml) in a 25 ml flexible plastic bottle under an atmosphere of carbogen (95% $O_2$, 5% $CO_2$) for 40 min at 37° C. with vigorous shaking. Five milliliters of buffer was then added, and the cells were passed through a mesh screen. The cells were then allowed to stand for several minutes in a 15 ml plastic test tube at room temperature, floating, and the buffer underneath was removed. This procedure (suspension, floating, and removal of buffer underneath) was repeated three times.

Adipocyte suspensions ($3\times10^5$ cells/ml) were divided into plastic vials (0.5 ml per vial) and incubated for 60 min at 37° C. under an atmosphere of carbogen with 0.2 mM [U-$^{14}$C] glucose, in either the absence or presence of insulin. Lipogenesis was terminated by adding toluene-based scintillation fluid (1.0 ml per vial) and the radioactivity in extracted lipids was counted (Moody et al., 1974). In a typical experiment insulin-stimulated lipogenesis was 4–5 fold higher than basal (basal "2000 cpm per $3\times10^5$ cell/h; $V_{insulin}$ 8,000–10,000 cpm per $3\times10^5$ cells/h). In this assay insulin stimulates lipogenesis with $ED_{50}$ value=0.15±0.03 ng/ml (Shechter and Ron, 1986). An insulin analog exhibiting $ED_{50}$ value=15 ng/ml is considered to have ~1% of the biological potency of the native hormone.

(iv) Receptor Tyrosine Kinase Activity Measurement

In this assay insulin activates its own receptor to phosphorylate a random copolymer containing L-glutamic acid and L-tyrosine at 4:1 molar ratio [Poly(Glu$_4$Tyr)]SEQ ID NO:1. The standard enzyme assay mixture (final volume 60 µl in 50 mM Hepes, pH 7.4–0.1% Triton X-100) contained WGA purified insulin receptor (5µg protein), 20 mM $MgCl_2$, 2 mM $MnCl_2$, 100 µM ATP and varying concentrations (from 1 ng/ml to 10 mg/ml) of insulin or insulin derivative. Following a 30 min preincubation at 22° C., the reaction was initiated by adding Poly(Glu$_4$Tyr) SEQ ID NO:1 (final concentration 0.7 mg/ml), it proceeded for 20 min at 22° C. and was terminated by adding EDTA (20 mM). Phosphotyrosine content in PolyGlu$_4$Tyr was quantitated by a radioimmunoassay procedure using specific monoclonal antibodies to phosphotyrosine (final dilution 1: 100,000) and $^{125}$I-BSA-phosphotyrosine conjugate. In this particular assay insulin facilitates half maximal effect at a concentration of 20±3 ng/ml. An insulin analog exhibiting $ED_{50}$ value=2 mg/ml is considered as having ~1% the biological potency of the native hormone.

Example 1

Preparation of N-Fmoc-insulin Derivatives (a) Synthesis

Human insulin (100 mg, 17.2 µmoles) (kindly donated by Biotechnology-General, Rehovot, Israel) was suspended in 4 ml of analytical grade dimethylformamide (DMF) containing 17.4 mg (172 µmoles) triethylamine. Fmoc-OSu (58 mg, 172 µmoles) was then added. The homogeneous reaction mixture was stirred at 25° C. for 20 hours and ethylacetate was then added until the solution became turbid, followed by the addition of ether to complete precipitation. The solvent was removed by centrifugation and the precipitate washed twice with ether and twice with water. This procedure yielded a mixture of mono, di and tri-N-Fmoc-insulin derivatives which were separated and purified by preparative HPLC. The monomodified N-Fmoc-insulin derivatives can be separated from the di and tri modified derivatives by washing the crude solid with isopropanol.

(b) Isolation and Purification of N-Fmoc-insulin Derivatives

The crude solid was subjected to reversed-phase HPLC (Spectra-Physics SP 8800 liquid chromatography system) equipped with HPLC prepacked column (Merck, LIChros-CART 250-10 mm containing LIChrosorb RP-18 [7 µm]. A linear gradient was formed from 0.1% trifluoroacetic acid (TFA) in $H_2O$ (solution A) and 0.1% TFA in acetonitrile:$H_2O$, 75:25 (solution B). The flow rate was 1 ml/min. The N-(Fmoc)$_1$-insulin derivatives emerged from the column with retention times of 21.1, 21.9 and 22.8 min, the N-(Fmoc)$_2$-insulin derivatives with retention times of 26.3, 27.1 and 27.7 min, and the N-(Fmoc)$_3$-insulin with retention time of 31.5 min. The fractions corresponding to 21–23 min, 26–28 min and 31.5 min were pooled, lyophilized and chemically characterized. The fractions corresponding to 21–23 min (monomodified insulins) and to 26–28 min (dimodified insulins) were further purified to the individual mono-Fmoc and di-Fmoc-insulin derivatives, respectively. Amounts of Fmoc groups attached to the insulin molecule were determined spectrophotometrically at 301 nm, following treatment of known amounts of N-Fmoc-insulin derivatives with 50% piperidine in $CH_2Cl_2$.

(c) Chemical Characterization of N-Fmoc-insulin Derivatives

Following preparative separation by HPLC procedure, seven N-Fmoc-insulin derivatives were obtained. This includes three monomodified, three dimodified and one trimodified derivative, respectively (Table I). The retention times and the yields of each individual compound is given in Table I. The different N-Fmoc-insulins can be readily resolved from each other and obtained in purified form under the experimental conditions applied here. Phe$^{B1}$, Lys$^{B29}$-N-(Fmoc)$_2$-insulin (retention time=27.7 min) and Gly$^{A1}$, Phe$^{B1}$, Lys$^{B29}$-N-(Fmoc)$_3$-insulin were characterized by several procedures including mass spectra (Table I).

(d) Synthesis of Phe$^{B1}$, Lys$^{B29}$-N-(Fmoc)$_2$-insulin,

Since the bioassays revealed that Phe$^{B1}$, Lys$^{B29}$-N-(Fmoc)$_2$-insulin is especially suited as a long-acting insulin, an alternative procedure was designed for synthesizing it. The Gly$^{A1}$ moiety was specifically protected with the t-Boc group under designed experimental conditions, using one equiv of di-tert-butyldicarbonate and DMSO/Et$_3$N, 20:1, as a solvent. Following separation by HPLC procedure, Gly$^{A1}$-N-Boc-insulin was reacted with excess of Fmoc-OSu (10 equiv), using DMF as a solvent and DIEA as a base. Treatment with TFA and purification on HPLC produced Phe$^{B1}$, Lys$^{B29}$-N-(Fmoc)$_2$-insulin, in a good yield (~50%).

(e) Biological Characterizations of N-Fmoc-insulin Derivatives

Several features of the N-Fmoc-insulin derivatives of the present invention are summarized in Tables II and III. Solubility of the derivatives in aqueous solutions decreased with increased modification. N-(Fmoc)$_1$-insulin are only slightly less soluble than native insulin whereas N-(Fmoc)$_3$-insulin is about 20 fold less soluble than the native hormone. The biological potencies decreased as well with increased derivatization. Thus, mono, di and tri-N-Fmoc-insulins exhibit 40–80%, 2–9% and <1% of the native insulin biological potency, respectively, as judged by [poly (Glu$_4$Tyr)]SEQ ID NO:1 phosphorylating assay. According to the more sensitive biological assay of lipogenesis with intact rat adipocytes, the Fmoc-insulin derivatives exhibit much lower biological potencies. Thus, Gly$^{A1}$-N-Fmoc-insulin and di-N-Fmoc-insulins exhibit 4.7% and 0.4–1.4% of the native insulin biological potency, respectively, using the lipogenesis assay (Table III). All seven derivatives are reverted into the native hormone upon incubation for 2 days at pH 8.5. This was proved both by regaining the full biological potency (Tables II and III) and by disappearance of the peaks of the derivatives, along with the appearance of the native hormone peak (retention time=15 min) upon separation by analytical HPLC procedure.

TABLE I

Chemical characterization of N-Fmoc-insulin derivatives

| Derivative | Retention time (HPLC), minutes[a] | Yield[b] (%) | Fmoc/mole insulin | Position of Fmoc insertion | Mass spectra (molecular weight) calculated | found [M + H]$^+$ |
|---|---|---|---|---|---|---|
| N-(Fmoc)$_1$-insulin | 21.1 | 3 | 0.8 | Gly$^{A1}$ | | |
| N-(Fmoc)$_1$-insulin | 21.9 | 6 | 1.2 | Lys$^{B29}$ | | |
| N-(Fmoc)$_1$-insulin | 22.8 | 4 | 0.9 | Phe$^{B1}$ | | |
| N-(Fmoc)$_2$-insulin | 26.3 | 12 | 1.7 | Gly$^{A1}$, Lys$^{B29}$ | | |
| N-(Fmoc)$_2$-insulin | 27.1 | 6 | 2.1 | Gly$^{A1}$, Phe$^{B1}$ | | |
| N-(Fmoc)$_2$-insulin | 27.7 | 14 | 1.9 | Phe$^{B1}$, Lys$^{B29}$ | 6252 | 6255 |
| N-(Fmoc)$_3$-insulin | 31.5 | 30 | 3.4 | Gly$^{A1}$, Lys$^{B29}$, Phe$^{B1}$ | 6474 | 6475 |

Note:
Amino acid analysis was used to verify the correct composition of all the Fmoc-derivatives.
[a]Established with Merck, LiChrospher 100 RP-8 (5 μm) column, employing a linear gradient formed from 60% solution A (0.1% TFA in water) and 40% solution B (0.1% TFA in acetonitrile:water, 75:25), to 100% solution B in 40 minutes (flow rate of 1 ml/min).
[b]Based on pure material obtained following HPLC.

TABLE II

Several representative features of Fmoc-insulin derivatives

| Derivative | Origin | Position of Fmoc insertion | Appearance in aqueous buffer (pH 7.4) | Solubility in aqueous buffer (pH 7.4, mg/ml) | Biological potency (%) | Biological potency following incubation (2 days, 37° C., pH 8.5) |
|---|---|---|---|---|---|---|
| Native insulin | human | | clear | ~4 or higher | 100 | 100 |
| N-(Fmoc)$_1$-insulin | human | Gly$^{A1}$ | nearly clear | ~3 | 40 ± 2 | 95 |
| N-(Fmoc)$_1$-insulin | human | Lys$^{B29}$ | nearly clear | ~3 | 78 ± 4 | 94 |
| N-(Fmoc)$_1$-insulin | human | Phe$^{B1}$ | nearly clear | ~3 | 76 ± 4 | 95 |
| N-(Fmoc)$_2$-insulin | human | Gly$^{A1}$, Lys$^{B29}$ | cloudy | ~2 | 2 ± 1 | 93 |
| N-(Fmoc)$_2$-insulin | human | Gly$^{A1}$, Phe$^{B1}$ | cloudy | ~2 | 3 ± 1 | 97 |
| N-(Fmoc)$_2$-insulin | human | Phe$^{B1}$, Lys$^{B29}$ | cloudy | ~2 | 9 ± 2 | 95 |
| N-(Fmoc)$_3$-insulin | human | Gly$^{A1}$, Lys$^{B29}$, Phe$^{B1}$ | very cloudy | ~0.2 | <1 | 98 |

Note:
Insulin-like potency was determined by both biological assays described in the experimental part.

TABLE III

Biological potencies and time course of activation of several N-Fmoc insulins using lipogenetic assay (with intact rat adipocytes)

| Derivative | ED$_{50}$ lipo-genesis ng/mL | Relative bio-logical potency (%) | Activity following incubation at pH 8.5, 37° C. (%) 9 hrs | 20 hrs | 45 hrs |
|---|---|---|---|---|---|
| Native insulin | 0.2–0.4 | 100 | | | |
| Gly$^{A1}$-N-Fmoc-insulin | 7 | 4.7 | 50 | 100 | |
| Gly$^{A1}$, Lys$^{B29}$-N-(Fmoc)$_2$-insulin | 44 | 0.4 | 10 | 20 | 97 |
| Gly$^{A1}$, Phe$^{B1}$-N-(Fmoc)$_2$-insulin | 30 | 1.1 | 18 | 40 | 100 |
| Phe$^{B1}$, Lys$^{B29}$-N-(Fmoc)$_2$-insulin | 12.3 | 1.4 | 10 | 20 | 98 |

Example 2
Biological Activity of N-Fmoc-insulins
(a) Time Course of Activation of N-Fmoc-insulins at pH 7.4

Prior to studying the antidiabetic potencies of N-Fmoc-insulins in diabetic rats, their rate of reactivation (which represents their conversion to the native hormone) was tested in the test tube. The derivatives have been dissolved in Hepes-buffer (50 mM, pH 7.4) containing 10% dimethylsulfoxide (DMSO) and incubated at 37° C. (i.e. at physiological pH and body temperature). At the indicated time points aliquots were withdrawn for determining the biological potency relative to native insulin. Biological activities were evaluated by Insulin receptor tyrosine kinase activation (a cell free assay as described in Biological Procedures above, section (iv)) and by stimulation of lipogenesis in intact rat adipocytes as described in Biological Procedures, section (ii). The results are shown in FIG. 1. Half maximal activation occurred for N-(Fmoc)$_3$-insulin at $t_{1/2}$=14 days and nearly full activation was evident following 21 days of incubation.

As a rule, the activation rate of N-(Fmoc)$_2$-insulin at pH 7.4 was faster. The six day lag period observed with N-(Fmoc)$_3$-insulin was not seen with N-(Fmoc)$_2$-insulin. Thus N-(Fmoc)$_3$-insulin appears to have a slower hydrolyzable Fmoc moiety that limits reactivation of the analog. Following its hydrolysis, the rate of activation is increased. From a practical viewpoint it implies that the mixture of the two analogs may release active insulin over a prolonged period of time, by covering earlier and later time periods. The relatively active monomodified Fmoc-insulin regained full biological potency at pH 7.4 with $t_{1/2}$=5 days.

Once arriving at the circulation N-(Fmoc)$_2$- and N-(Fmoc)$_3$-insulins are expected to provide a low basal concentration of the hormone over prolonged periods. This may be primarily dictated by the rate of conversion of the inactive derivative into the active short-lived native hormone. Fortunately, the N-(Fmoc)$_{2,3}$-insulins exhibit slow rates of activation (as shown in FIG. 1). A rapid (sudden) rate (i.e. within minutes rather than hours) could have been resulted in hypoglycemic episodes Phe$^{B1}$, Lys$^{B29}$-N-(Fmoc)$_2$ insulin is 9% biologically active, as determined by the [poly (Glu$_4$Tyr)]SEQ ID NO:1 phosphorylating assay, and exhibits intermediate solubility between the native and N-(Fmoc)$_3$-insulin. Unlike N-(Fmoc)$_3$-insulin, the conversion of (N-Fmoc)$_2$-insulin to the native hormone starts shortly (within hours) after incubation, as shown in FIG. 1. Thus, N-(Fmoc)$_2$-insulin (being a priori more active) is expected to have a faster onset of action following administration. Thus, a proper combination of N-(Fmoc)$_2$- and (N-Fmoc)$_3$-insulins can make the ideal formula for basal insulin release that is characterized by rapid onset and long duration of action, following a single administration, and constitutes one preferred embodiment of the invention.

TABLE IV

Effect of a single administration of Phe$^{B1}$, Lys$^{B29}$-N-(Fmoc)$_2$-insulin on daily weight gain of STZ rats.

| Group | Description | Daily weight gain gram/rat (over the first three days) |
|---|---|---|
| A (n = 5) | STZ rats which received vehicle only (2.0 ml, 20% DMSO/rat) | 2.0 ± 0.2 |
| B (n = 5) | STZ rats which received a single s.c. administration of NPH-human insulin (Humulin N) (3 mg/rat) | 12.0 ± 2 |
| C (n = 5) | STZ rats which received a single s.c. injection of N-(Fmoc)$_2$ insulin (3 mg/rat) | 11.5 ± 1.3 |

Figure 2:
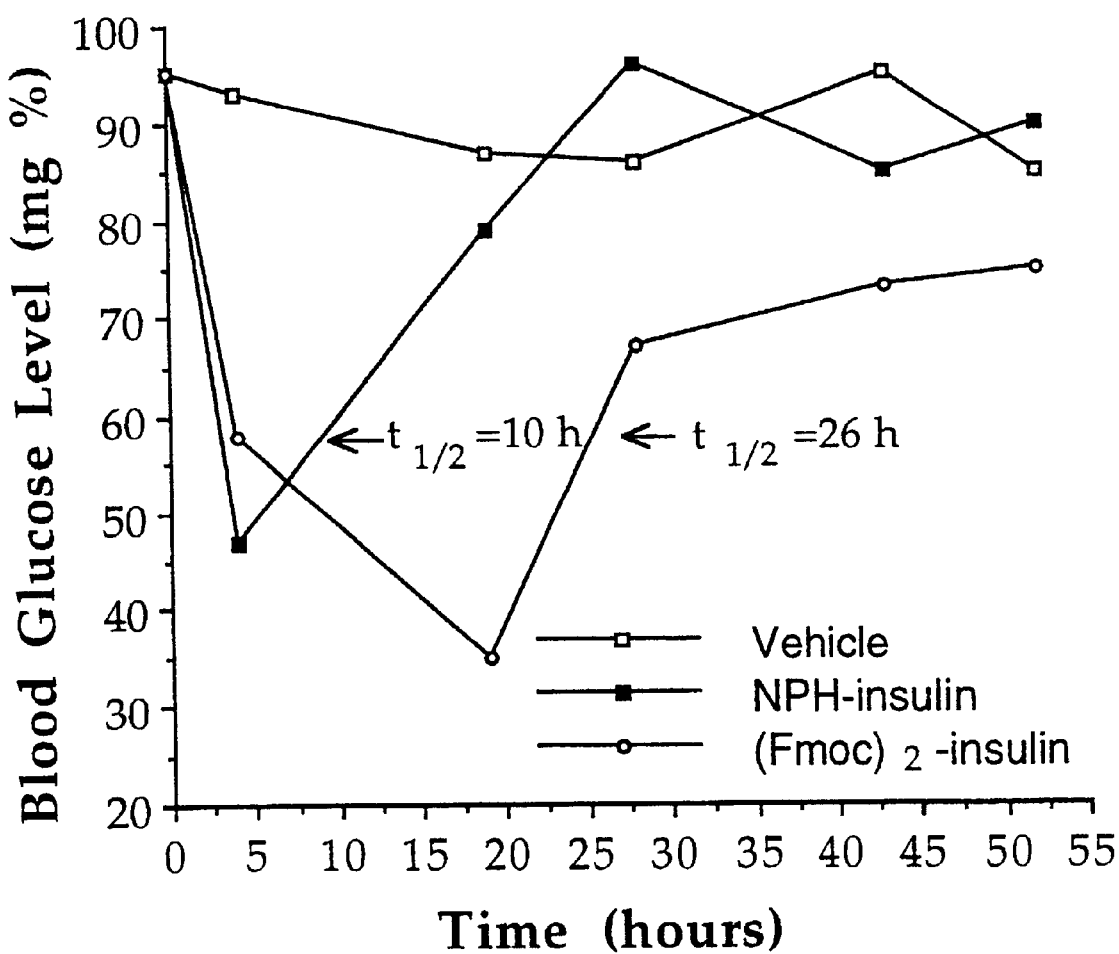
FIG. 2 shows the effect of a single intraperitoneal administration of (Fmoc)$_2$-insulin (3 mg/rat in 2 ml 10% DMSO) and NPH-insulin (3 mg/rat) on blood glucose level of normal rats.

(b) Effect of a Single Intraperitoneal Administration of Phe$^{B1}$, Lys$^{B29}$-N-(Fmoc)$_2$-insulin to Normal Rats In order to further confirm that the long-acting capacity of (Fmoc)$_2$-insulin is due to its slow conversion to the native hormone under physiological conditions, an additional in vivo assay has been designed. This assay reflects the post-subcutaneous long-acting feature of insulin (or insulin derivatives) within the circulation. Normal rats received a single intraperitoneal injection of native insulin, NPH-insulin and (Fmoc)$_2$-insulin (3 mg/rat), and their blood glucose levels were monitored over a period of three days. The results are shown in FIG. 2. Thus, native insulin (FIG. 3) and NPH-insulin (FIG. 2) induced hypoglycemia over a period of about 12 and 15 hours, respectively. Recovery from hypoglycemia occurred with $t_{1/2}$ of 8 and 10 hours, respectively. (Fmoc)$_2$-insulin reduced blood glucose levels over a period of about 48 hours, and recovery from hypoglycemia occurred with $t_{1/2}$ of 26 hours. These results supported our notion that indeed the prolonged action of (Fmoc)$_2$-insulin is emerging from its intrinsic characteristics, and not due to the conventional mechanism of NPH-insulin, i.e. precipitation at the injection site and its slow dissolution-entrance to the circulation. As expected, the differences in the capacities of native insulin and NPH-insulin to reduce blood glucose levels in this assay are minor as compared to their administration by the subcutaneous mode. This fact is due to the large volume of liquids existing in the peritoneal cavity and hence fast conversion of the Zn-crystalline insulin to yield the monomeric form. The two other (Fmoc)$_2$-insulin derivatives, [Gly$^{A1}$, Lys$^{B29}$] and [Gly$^{A1}$, Phe$^{B1}$], were synthesized and also evaluated in this assay. Results (not shown) exhibited similar long-acting pattern as for Phe$^{B1}$, Lys$^{B29}$-N-(Fmoc)$_2$-insulin, with $t_{1/2}$ of 22–24 hours for both derivatives.

(c) N-(Fmoc)$_3$ Insulin is Resistant to Proteolysis

Figure 4:
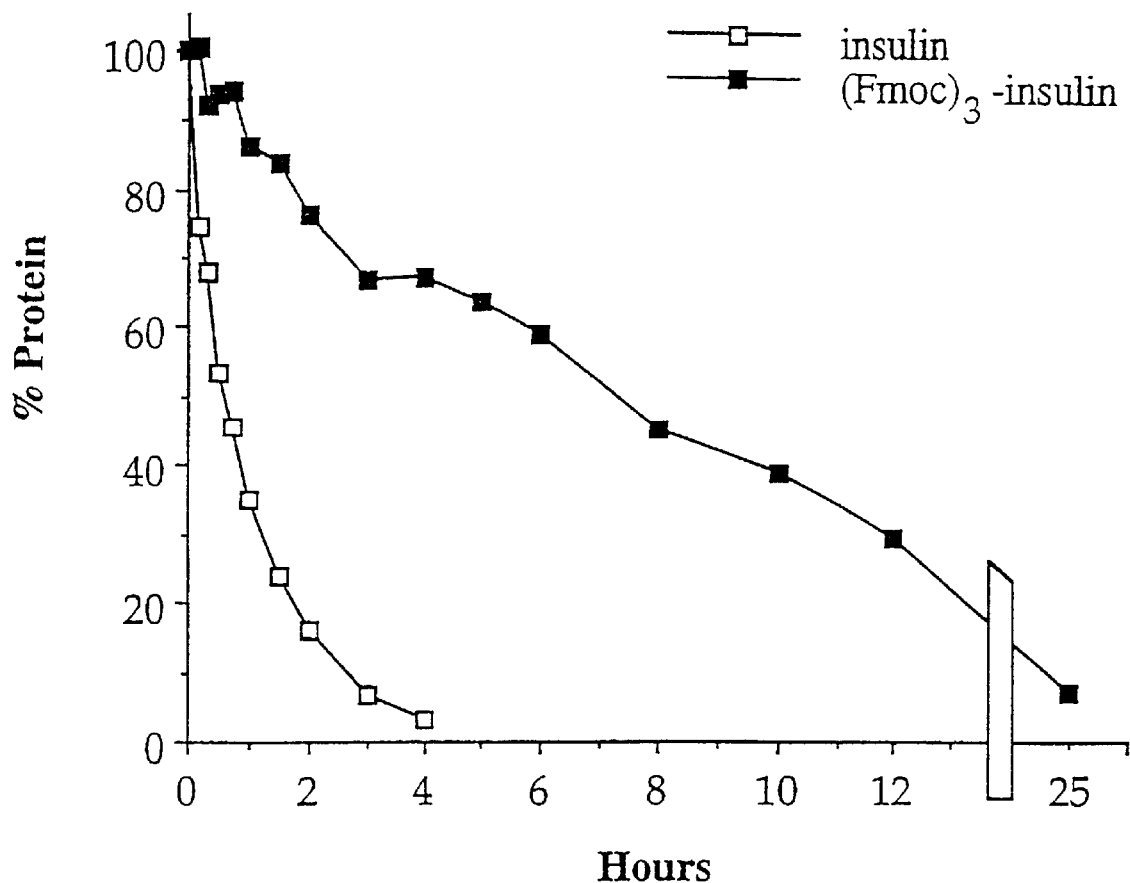
FIG. 4 shows degradation of insulin (open squares) and $Gly^{A1}$, $Phe^{B1}$, $Lys^{B29}$-N-(Fmoc)$_3$-insulin (closed lozenges) by a mixture of trypsin and chymotrypsin.

Native insulin or N-(Fmoc)$_3$-insulin (1 mg/ml of each in 50 mnM Hepes, pH 7.4, 10% DMSO) were incubated at 37° C. Chymotrypsin and trypsin (0.5% w/w, of each) was then added. At the indicated time points aliquots were withdrawn and subjected to analytical HPLC procedure. Percent degradation was determined by the decrease in area of the native insulin peak (retention time 15 min) and of the N-(Fmoc)$_3$-insulin peak (retention time 31.5 min). The results are shown in FIG. 4.

N-(Fmoc)$_3$ insulin was found to be highly resistant to proteolysis by a mixture of chymotrypsin and trypsin at pH 7.4. Proteolysis proceeded with $t_{1/2}$ values of 0.5 and 7.5 hours for the native and N-(Fmoc)$_3$ insulin, respectively.

Example 3
Effect of a Single Subcutaneous Administration of Phe$^{B1}$, Lys$^{B29}$-N-(Fmoc)$_2$- and N-(Fmoc)$_3$ Insulin to STZ-diabetic Rats The STZ rat is an excellent model for evaluating in vivo insulin therapy. In this model about 90% of the β-cell function has been destroyed by streptozotocin, as judged by histological studies (as described by Pederson et al., 1989). The rats are hypoinsulinemic (having 10–30% of the normal insulin level), hyperglycemic (>300 mg/dl; normal glucose level of control rats is 90–100 mg/dl), and catabolic. Visible external symptoms are 'sick' appearance and three to four fold increase in fluid intake and urine excretion. Daily weight gain is decreased to 10–20% (0.3–0.8 g/day/rat) of the normal weight gain of control rats. The pathological changes in tissues of STZ-rats are enormous. Some of the more prominent biochemical alterations are decreased activity of key enzymes of glycogen metabolism, depletion in liver glycogen, a decrease in number of glucose transporters, in peripheral tissues, and an increase in insulin binding capacity that is not accompanied with an increase in responsiveness to insulin.

In this diabetic rat model a convenient insulin therapy is the continuous administration of insulin (5 units/day/rat) over a period of one week. This treatment normalizes blood glucose levels, returns diabetic rats into anabolic state, and ameliorates many of the pathological effects induced by hyperglycemia and hypoinsulinemia. A single administration of rapid-acting (regular) insulin is effective over a period of several hours only. Also, following termination of the seven day therapy protocol, hyperglycemia reoccurs within 24–30 hours.

To evaluate whether N-(Fmoc)$_3$-insulin has prolonged antidiabetic effect, STZ-rats, two weeks after induction of diabetes, were administered either a single subcutaneous injection of native insulin (Group A, 25 units, 1 mg, dissolved in 1.0 ml H$_2$O–10% DMSO, n=4), or of N-(Fmoc)$_3$-insulin (Group B, 1 mg, dissolved in 1.0 ml H$_2$O-10% DMSO, n=4). Blood glucose levels and daily weight gains were followed over a period of seven days.

Figure 5:
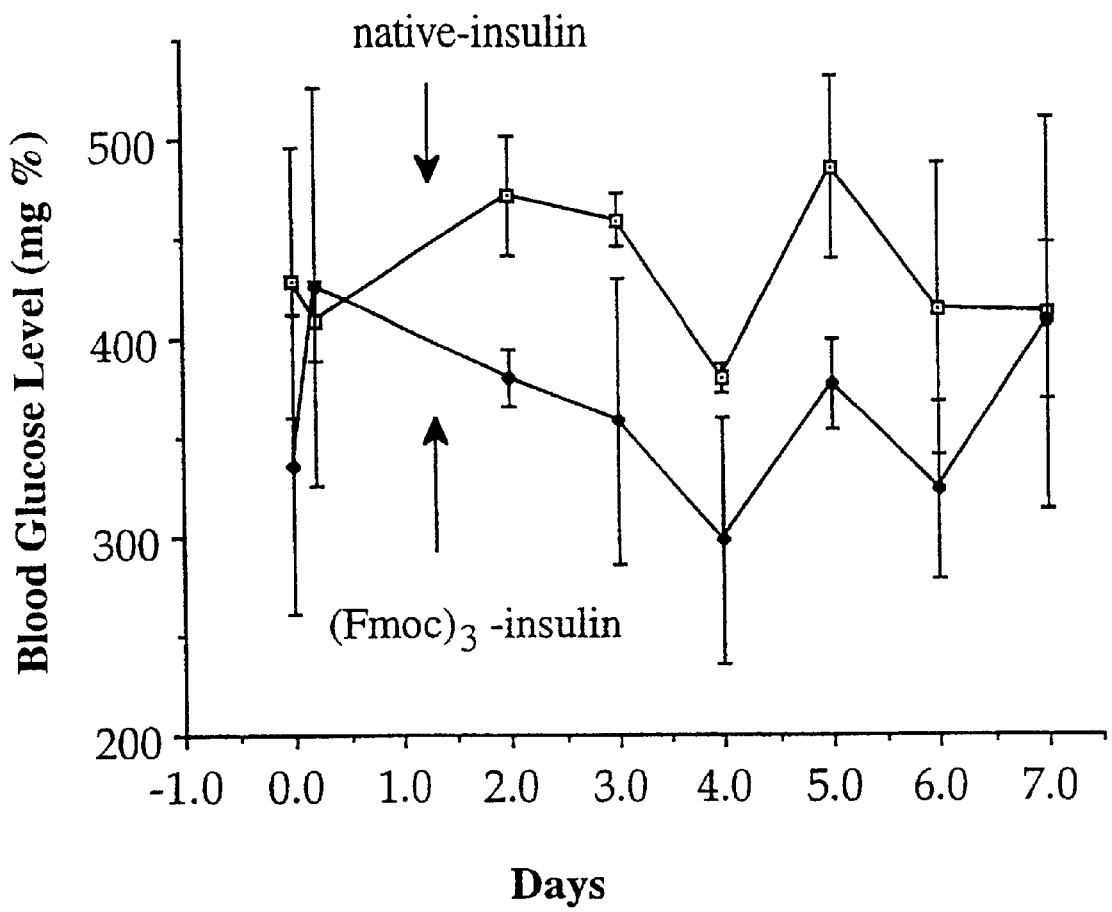
FIG. 5 shows the effect of a single $Gly^{A1}$, $Phe^{B1}$, $Lys^{B29}$-N-(Fmoc)$_3$-insulin administration (closed circles) on blood glucose levels of diabetic streptozotocin (STZ)-treated rats in comparison to native insulin administration (open squares).

The results are shown in FIG. 5. Each point represents the arithmetic mean±SEM of plasma glucose for 4 rats. Circulating glucose levels in Group B were significantly lower. Thus, glucose levels were 90–110 mg/dl lower in Group B, starting from day two following administration, and these lower glucose levels existed up to day six. On day seven, there was no significant difference between the two groups of rats in circulating glucose levels. The rats receiving N-(Fmoc)$_3$ insulin had a 'healthier' appearance. Daily weight gains were nearly three times higher in Group B and amounted to 0.57±0.08 and 1.43±0.14 g/rat/day, in Groups A and B, respectively (not shown). Thus, a single administration of N-(Fmoc)$_3$-insulin gave prolonged and satisfactory antidiabetic actions lasting over a period of four days (following a delayed onset of approximately two days). This long-lasting effect in vivo may be explained by the ability of the derivative to escape receptor-mediated endocytosis and also by its resistance to proteolysis. In addition N-(Fmoc)$_3$-insulin is largely insoluble in aqueous solutions. Thus, in humans, the overall lasting effect may proceed by substitution of the old therapeutic principle, i.e. gradual dissolution of 'built-in' insoluble insulin, following subcutaneous administration together with the new principle, namely, circulating long-living covalently modified inactive insulin derivative, that is slowly converted into the native hormone. As this insulin derivative is inactive, larger doses can be administered with no fear of hypoglycemic episodes.

To test the effect of Phe$^{B1}$, Lys B$^{B29}$-N-(Fmoc)$_2$-insulin in lowering blood glucose levels in experimental diabetic rats, STZ-treated rats, 9 days after induction of diabetes, received either a single s.c. injection of the N-(Fmoc)$_2$-insulin (Group A, 3 mg/rat, in 2.0 ml 20% DMSO, n=5), or a single s.c. injection of long-acting insulin (NPH-human insulin, Humulin N, HI-310) (Group B, 0.75 ml (3 mg) per rat, n=5). Group C (n=5) received the vehicle only (2.0 ml of 20% DMSO). Blood glucose levels were determined daily.

Figure 6:
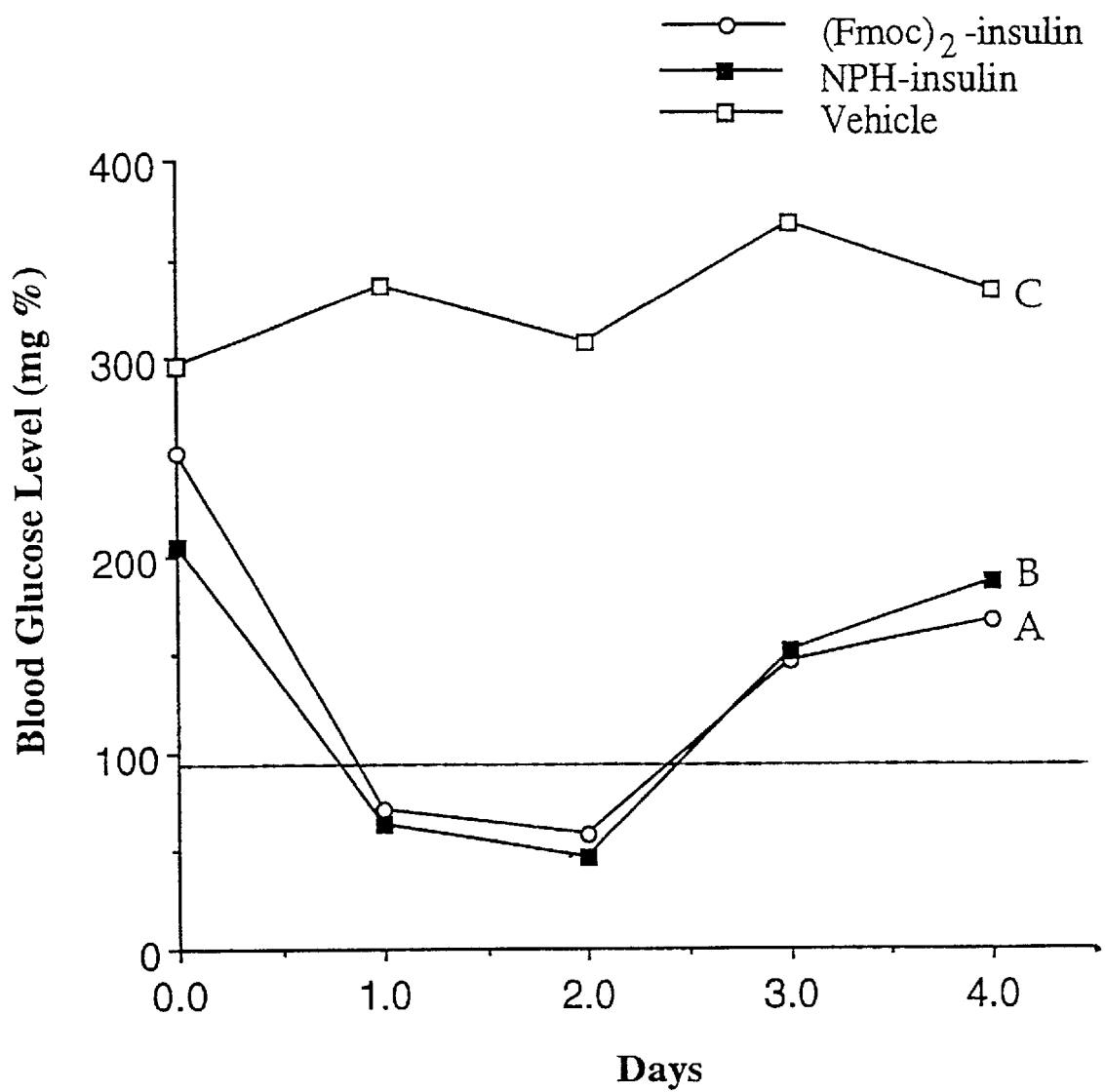
FIG. 6 shows that a single administration of $Phe^{B1}$, $Lys^{B29}$-N-(Fmoc)$_2$-insulin to STZ-treated-hyperglycemic rats induces prolonged effect in lowering blood glucose levels.

The results are shown in FIG. 6 in which the horizontal dashed line indicates the arithmetic mean of plasma glucose for control rats. As shown in FIG. 6, a single subcutaneous administration of HPLC-purified Phe$^{B1}$, Lys B$^{B29}$-N-(Fmoc)$_2$-insulin induced normoglycemia over a period of 4 days and increased daily weight gain of these catabolic STZ-rat models (Table III). N-(Fmoc)$_2$-insulin was as effective as the commercially available (insoluble) long-acting preparation. Rapid-acting (soluble) insulin is effective in lowering blood glucose levels in this experimental system over a period of several hours only (not shown). This preparation is fairly soluble in aqueous solution (at pH 7.4), a fact that may be advantageous over the insoluble N-(Fmoc)$_3$-insulin, because suspensions cannot be accurately administered by s.c. injection.

Example 4
Preparation and Biological Activity of (2-sulfo)Fmoc-insulin (a) Synthesis of (2-sulfo)Fmoc-insulin (Sulfmoc-insulin)

The Fmoc group itself was modified in order to reduce Fmoc-insulin's hydrophobicity and consequently to increase its solubility in aqueous buffers, as well as to modify the rate of reconversion to insulin. This can be done by introducing polar or, preferably, charged groups into the fluorene ring, such as halogen, nitro, carboxyl, amino, ammonium, and sulfo groups. In electrophilic substitution reactions, fluorene is first attacked at the 2 position and, generally, the nature of the substituent at position 9 (e.g. CH$_2$OCO-OSu) has no effect on the orientation of the substitution. Thus, treatment of Fmoc-OSu with 0.9 equiv of chlorosulfonic acid in dichloromethane (DCM) at 0° C., gave (2-sulfo)Fmoc-OSu in high yield (formula (i), R$_1$=SO$_3$H at position 2, R$_2$=R$_3$=R$_4$=H, A=OCO-OSu). Treatment with more than 1 equiv will result in substitution also at position 7 of the fluorene ring.

The (2-sulfo)Fmoc groups were introduced into insulin by coupling of the active (2-sulfo)Fmoc-OSu ester to the amino groups of insulin. Reaction was carried out in aqueous buffers (pH 7.4) and excess reagent (~20 equiv). Following dialysis and lyophilization the product was turned to be water soluble. HPLC analysis showed predominance of one main product, apparently (Sulfmoc)$_2$-insulin, as determined by mass-spectra (m/z 6411). When the reaction was carried out in acetonitrile/water, 1:1, the main product was (Sulfmoc)$_3$-insulin, as determined by mass-spectra (m/z 6713).

(b) Time Course of Activation of (2-sulfo)Fmoc-insulin

The (Sulfmoc)$_2$-insulin was fully reverted into the native hormone upon incubation at 37° C. for 36 hours at pH 8.5 (0.1 M NaHCO$_3$), or for 10 days at pH 7.4 (50 mM Hepes buffer) with t$_{1/2}$ values of 12–15 hours and 6 days, respectively. This was proved by disappearance of the peak of the insulin derivative, along with the appearance of the peak of the native hormone, using analytical HPLC procedure. Note that hydrolysis of (Sulfmoc)$_2$-insulin to the native hormone is faster as compared to the hydrolysis of (Fmoc)$_2$-insulin (21 days at pH 7.4, 37° C.).

(Sulfmoc)$_2$-insulin is 0.5% biologically active and exhibits good solubility in water. Upon incubation at pH 8.5, 37° C., (Sulfmoc)$_2$-insulin returns to fully-active native insulin with t$_{1/2}$ value of 4–6 hours as judged by time-dependent increase in biological potency (assay of lipogenesis in rat adipocytes).

Figure 3:
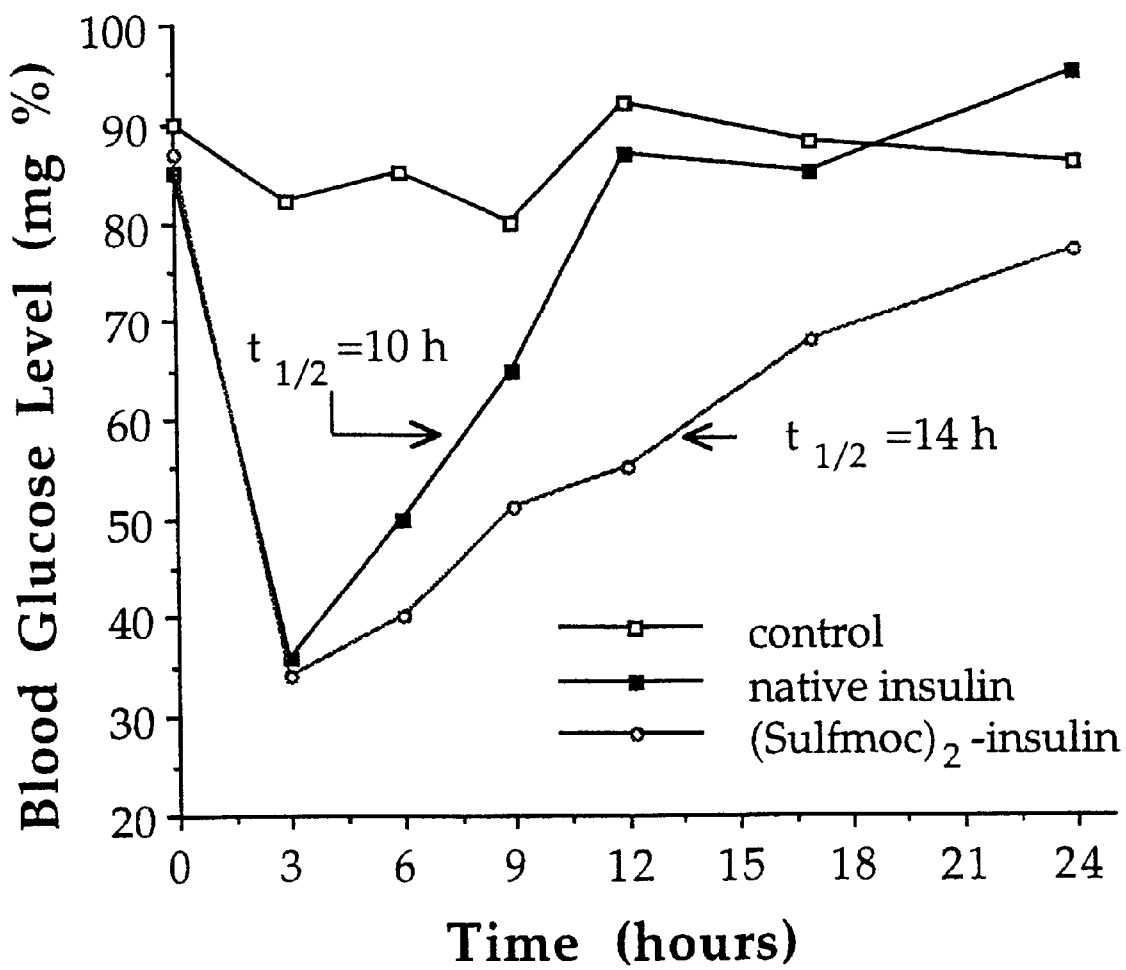
FIG. 3 shows the effect of a single intraperitoneal administration of (Sulfmoc)$_2$-insulin and native insulin (both 3 mg/rat in 1 ml water) on blood glucose level of normal rats.

(c) Effect of a Single Intraperitoneal Administration of (2-sulfo)Fmoc-insulin to Normal Rats To evaluate the long-acting capacity of (Sulfmoc)$_2$-insulin, downstream to subcutaneous absorption, normal rats were received a single intraperitoneal injection of native insulin, NPH-insulin, or (Sulfmoc)$_2$-insulin. Blood glucose levels were followed for two days. FIG. 3 shows that (Sulfmoc)$_2$-insulin induced hypoglycemia over a period of 24 hours. Recovery from hypoglycemia occurred with t$_{1/2}$ value=14 h. In case of rapid and NPH-insulin, these t$_{1/2}$ values amounted to 8 (FIG. 3) and 10 hours (FIG. 2), respectively. Thus, a single administration of (Sulfmoc)$_2$-insulin gave an intermediate anti-diabetic action, that is 1.5–2 fold longer than that of rapid or NPH-insulin. These results agree with the accelerated rate of hydrolysis of Sulfmoc-insulin previously found in vitro. Thus, the sulfonic acid group at position 2 of the fluorene ring increased the rate of proton abstraction at position 9 and therefore the hydrolysis of the Sulfmoc moiety, by 2–3 fold. Earlier studies performed on the lability of the Sulfmoc group to various bases, showed greater base sensitivity than the parent system. In addition, rate constant for the release of the Sulfmoc group from glycine, for example, was much higher than the Fmoc group (factor of about 30). Therefore, increase of solubility by introducing the Sulfmoc group into insulin, reciprocally decrease the long-lasting effect of this derivative. Thus, the principle of long-lasting anti-diabetic effect, through escaping receptor-mediated endocytosis and degradation, holds for the sulfonic-insulin derivative as well.

The enhanced rate of the removal of the Sulfmoc group from insulin may be advantageous in certain applications of insulin administration such as intermediate preparations. Such preparations will obviously have the benefit of being completely soluble in aqueous buffers, in contrast to the available commercial preparations. Moreover, other groups, with diverse acidities or polarities can be introduced to the fluorene ring. Therefore, controlling of the type and number of groups introduced to the Fmoc group, can determine the degree of solubility and the rate of reactivation of the modified insulin.

Example 5
Preparation of Amino and Carboxyl-terminal Modified Insulin (N-Fmoc- and C-Fm-insulin) Derivatives N-(Fmoc)$_3$-insulin (64.5 mg; 10 μmol; 60 μmol of carboxylic moieties, i.e. pertaining to 4 intrachain Glu and two C-terminal residues) was dissolved in 8 ml of dimethylformamide (DMF) (Lab. Scan., Dublin, Ireland) along with o-nitrophenol (250 μmol; 35 mg) or N-hydroxysuccinimide (250 μmol; 28 mg) and the solution was cooled to 4° C. A solution of N,N-dicyclohexylcarbodiimide (DCC; 250 mmol, 53 mg) in 0.5 ml of DMF was added and the reaction mixture was kept 1 h at 4° C. and then 6 h at room temperature. Precipitated N,N-dicyclohexyl urea was removed by centrifugation and the o-nitrophenyl or N-hydroxysuccinimide esters, respectively, of N-(Fmoc)$_3$-insulin were precipitated by dry, ice cold, ether. The solid was washed twice with dry ether, dried and dissolved in 8 ml of DMF. A a solution of 9-fluorenylmethanol (250 μmol; 50 mg) and imidazole (250 μmol; 17 mg) in 1 ml DMF was added. The reaction mixture was allowed to stand overnight at room temperature. Precipitation with dry ether afforded 62 mg of N-(Fmoc)$_3$, C-(Fm)$_n$-insulin. The main reaction product was the hexa-9-fluorenylmethyl ester C-(Fm)$_6$ of N-(Fmoc)$_3$-insulin (n=6).

Example 6
Preparation of Carboxyl-terminal Fm-insulins (C-Fm-insulins)

For the preparation of t-butyloxycarbonyl (t-Boc)$_3$-insulin, di-tert-butyldicarbonate (56 mg, 258 μmole) was added to an ice-cooled, stirred suspension of insulin (100 mg, 17.2 μmole) and triethylamine (174 mg, 172 μmole) in DMF (4 mL), The reaction mixture was allowed to warm to room temperature and stirred for 5 h (gradually becoming clear). Ethyl acetate was then added until the solution became turbid, followed by addition of ether, and the precipitate was centrifuged and washed twice with ether. The resulting crude solid (95 mg) was utilized further without any purification. Analytical HPLC showed one main product that eluted at 27.5 min.

The product was dissolved in 10 ml of DMF and treated with o-nitrophenol or N hydroxysuccinimide, as above, to yield the corresponding active esters. These were reacted with 9-fluorenylmethanol, in the presence of imidazole, as above, and N-(t-Boc)$_3$, C-(Fm)$_n$-insulin was obtained as a powder (87 mg) after precipitation with dry ether. The powder was dried in vacuum over P$_2$O$_5$ and then treated for 1 h at room temperature with 5 ml of trifluoroacetic acid to effect removal of N-terminal t-Boc protecting groups. During this procedure, most of the insulin derivative dissolved. Addition of ice-cold dry ether led to a powder which was isolated by centrifugation and washed thoroughly with dried ether. Yield of a product, primarily C-(Fm)$_6$-insulin, was 79 mg.

Example 7
Preparation of (Fmoc)$_1$-Human Growth Hormone (Fmoc$_1$-hGH

Under normal physiological conditions, hGH levels in healthy subjects are increased daily in a pulsatile manner several times (at day and night). hGH is a short-lived species. The current therapeutic protocol includes a single daily injection of hGH and is likely to be effective for several hours only. A long-acting (slow-released) hGH preparation that supply a treshold-based level of hGH during 24 h hours of the day and night, is highly desirable.

Native hGH (Biotechnology General, Rehovot, Israel; 9.2 mg) was dissolved in 0.1 M NaHCO$_3$ (2.0 ml; pH 8.5), DMSO (0.1 ml) was added (final DMSO concentration. ~5%), and the solution was cooled to 0° C. One equivalent of Fmoc-OSu in 10 μl (taken from a stock solution of 18.5 mg/ml in DMSO) was then added, and the reaction proceeded for 30 min at 0° C., under moderate stirring. Another 10 μl (containing 1 equivalent of Fmoc-OSu) was then added, and after 30 min the mixture was dialyzed overnight at 7° C., against H$_2$O. Semi-preparative HPLC yielded two main protein peaks corresponding to native hGH (~20% of total; retention time 30 min; RP-8 column; 250×10 mm; Merck) and modified Fmoc-hGH (~80% of total; retention-time 32 min).

Table V shows conversion of Fmoc-hGH (1 mg/ml) to native hGH upon incubation at 37° C. in 0.1 M NaHCO$_3$ (pH 8.5). At the indicated time points, aliquots were withdrawn and subjected to analytical HPLC procedure (RP-8 column). Conversion of Fmoc-hGH to native hGH was evaluated by the increase in peak area corresponding to native hGH.

As shown in Table V, Fmoc-hGH has 15% of the native hormone's receptor-binding potency. Incubation of Fmoc-hGH at pH 8.5 (37° C.) for about 6 days or at pH 10.5 (37° C.) for four days yielded fully active, native hGH, as judged by HPLC analysis and by receptor binding assays.

TABLE V

Generation of native hGH from Fmoc-hGH upon incubation at 37° C.

| Compound | Treatment | Ability to displace iodinated hormone[1] (%) | Conversion to hGH[2] (%) |
| --- | --- | --- | --- |
| hGH |  | 100 |  |
| Fmoc-hGH |  | 15 |  |
| Fmoc-hGH | 1 day, pH 10.5 | 25 |  |
| Fmoc-hGH | 4 days, pH 10.5 | 100 |  |
| Fmoc-hGH | 1 day, pH 8.5 |  | 23 |
| Fmoc-hGH | 2 days, pH 8.5 |  | 62 |
| Fmoc-hGH | 6 days, pH 8.5 |  | 100 |

[1]Displacement of iodinated hGH was carried out according to Gertler et al., 1984. Native hGH was fully stable under the conditions applied to Fmoc-hGH (pH 10.5, 37° C., 4 days).
[2]Fmoc-hGH (1 mg/mL) was incubated at 37° C. in 0.1 M NaHCO$_3$ (pH 8.5). At the indicated time points, aliquots were withdrawn and subjected to analytical HPLC. Conversion of Fmoc-hGH to native hGH was evaluated by the increase in peak area corresponding to native hGH.

Example 8
Preparation of N-Fmoc-Cephalexin and Cephalexin-O-Fm Ester

Cephalexin [7-(D-α-aminophenylacetamido) desacetoxycephalosporanic acid] is a β-lactam antibiotic with a broad spectrum of activity against Gram (−) and Gram (+) bacteria. Two monosubstituted cephalexins were prepared by covalently attaching a fluorenylmethyl (Fm) moiety either to the amino group (N-Fmoc-cephalexin) or to the carboxylic group via esterification (cephalexin-O-Fm).

(i)(a) Preparation of N-Fmoc-cephalexin

To a stirred suspension of cephalexin hydrate (Sigma, USA; 50 mg, 0.144 mmole) and triethylamine (29 mg, 0.288 mmole) in dichloromethane (DCM; 2.5 ml), a solution of Fmoc-OSu (145 mg, 0.432 mmole) in DCM (2.5 ml) was added dropwise over 5 min. The reaction mixture, which became clear after 1 h, was stirred overnight at room temperature, during which it turned turbid. After concentration under vacuum, ether was added to the mixture, and the resulting precipitate was filtered and washed twice with ether. The filtrate was dissolved in DCM and extracted with acidified water (pH ~2), water and brine, and dried over anhydrous MgSO$_4$. After filtration and concentration of the solution, ether was added. The precipitated product was filtered and washed with ether to yield Fmoc-cephalexin as a pure product, as judged by TLC (1-butanol:acetic acid:water, 8:1:1) and by analytical HPLC procedure (eluted at 33 min, while under similar conditions native cephalexin is eluted at 6.5 min). Mass spectrum analysis (Fast Atom Bombardement, FAB) gave the expected molecular weight for N-Fmoc-cephalexin (M/Z 570.1 [M+H]$^+$).

(i)(b)Antibacterial Potency of Fmoc-cephalexin

For the determination of the antibacterial potencies of native cephalexin and Fmoc-cephalexin, tubes containing a dilute suspension of Staphylococcus aureus (0.5 ml/glass tube) were incubated for 6 hours at 37° C. in the absence and presence of increased concentrations of native cephalexin or Fmoc-cephalexin, prior to and subsequent to the treatment specified in air Table VI. At the indicated time points, aliquots were withdrawn and analyzed for their potency to arrest growth of *Staphylococcus aureus*. Bacterial growth was then evaluated by increased turbidity measured spectroscopically at 700 nm.

TABLE VI

Antibacterial potencies of native cephalexin and N-Fmoc-cephalexin

| Compound | Incubation at pH 7.4, 37° C. | Concentration inhibiting 50% of bacterial growth ($\mu$M) (IC$_{50}$) | Antimicrobial potency[1] (%) |
|---|---|---|---|
| native cephalexin | — | 0.9 | 100 |
| native cephalexin | 1 day | 1.5 | 100 |
| native cephalexin | 3 day | 5.3 | 100 |
| native cephalexin | 6 days | 18 | 100 |
| Fmoc-cephalexin | — | 23 | 6 |
| Fmoc-cephalexin | 1 day | 15 | 10 |
| Fmoc-cephalexin | 3 days | 9 | 59 |
| Fmoc-cephalexin | 6 days | 4.5 | 100 |

[1]Numbers refer to the potency of cephalexin employed as a control throughout the assays.

Incubations were performed at pH 7.4 with native cephalexin or with N-Fmoc-cephalexin (100 $\mu$g/mL) in 50 mM Hepes buffer, 20% DMSO.

As shown in Table VI, N-Fmoc-cephalexin is inactive (~6%). Preincubation over a period of 6 days (pH 7.4, 37° C.) generated native cephalexin as judged by HPLC monitoring, and by regaining about 50% of the antibacterial potency of the parent compound. Native cephalexin undergoes substantial time-dependent spontaneous inactivation upon incubation, whereas N-Fmoc-cephalexin is significantly more stable to the same conditions. Thus, the expected prolonged action of N-Fmoc-cephalexin in vivo is likely to originate both from higher chemical stability at physiological pH and temperature, as well as by escaping degradation. N-Fmoc-cephalexin is more stable to hydrolysis by penicillinase than the parent compound (not shown).
(ii) Preparation of Cephalexin-O-Fm Ester (Cephalexin Fluorenylmethyl Ester)
(a) N-Boc-cephalexin To an ice-cooled stirred suspension of cephalexin hydrate (50 mg, 0.144 mmole) and triethylamine (29 mg, 0.288 mmole) in DCM (3 ml), a solution of di-tert-butyl dicarbonate (94.2 mg, 0.432 mmole) in DCM (2 ml) was added. The reaction mixture was allowed to warm up to room temperature and stirred overnight, until no ninhydrin-positive starting material was observed by TLC (1-butanol:acetic acid:H$_2$O, 8:1:1). The reaction mixture was then diluted with DCM (2.5 ml), extracted with acidified water (pH~2), water and brine, and dried over anhydrous MgSO$_4$. After concentration, the product was precipitated with petroleum ether (b.p. 40–60° C.), filtered and washed again with petroleum ether. The product was homogeneous as confirmed by TLC and HPLC procedures.
(b) Cephalexin-O-Fm Ester To an ice-cooled stirred solution of N-Boc-cephalexin (25 mg, 0.056 mmole), 9-fluorenylmethanol (22 mg, 0.112 mmole) and 4-dimethylaminopyridine (13.7 mg, 0.112 mmole) in DCM (2 ml), a solution of DCC (23.1 mg, 0.112 mmole) in DCM (1 ml) was added dropwise over 20 min. The resulting mixture was stirred overnight at room temperature and the solution was filtered to remove dicyclohexylurea. The filtrate was diluted with DCM (2.5 ml) and then extracted twice with 1 M NaHCO$_3$ solution, 10% citric acid, water and brine, and dried over anhydrous MgSO$_4$. The solution was evaporated to yield an oily solid, which was triturated with petroleum ether to furnish the Boc-cephalexin-OFm product (as confirmed by TLC and HPLC). The Boc moiety was removed by dissolving the crude solid (25 mg) in 1 ml solution of TFA:DCM (1:1 v/v). After standing for 20 min at room temperature, the TFA was removed by evaporation and the solid residue dissolved in isopropanol which was then evaporated. This procedure was repeated twice. The crude solid was triturated with petroleum ether to form the final pure ester, as judged by both TLC and HPLC procedures.

Example 9

Preparation of di-9-(fluorenylmethoxycarbonyl)polymyxin B [(Fmoc)$_2$-PMXB]

Polymyxin-B (PMXB), a representative member of the family of cyclic-peptidic antibiotics, is effective against Gram (−) bacteria. PMXB contains 5 residues of diaminobutyric acid which can be modified by insertion of Fmoc groups using the reagent 4-(9-fluorenylmethoxycarbonyloxy)phenyl-dimethylsulfonium methylsulfate (Fmoc-DSP). The molar ratio of Fmoc-DSP reagent and peptide will determine the extent of modification of the PMXB molecule.

For the preparation of (Fmoc)$_2$-PMXB, to a stirred solution of PMXB (Sigma, USA: 10 mg, 7.2 $\mu$mole) and (Fmoc-DSP; 7.1 mg, 14.4 $\mu$mole) in H$_2$O (1 ml), a solution of NaHCO$_3$ (0.1 M, 0.15 ml) was added dropwise. The reaction mixture which gradually became turbid was stirred overnight, at room temperature. The resulting precipitate was centrifuged, washed twice with water, dissolved in a small volume of DMF and precipitated with ether to give white crude solid.

TABLE VII

Antibacterial potencies of (Fmoc)$_2$-PMXB and native PMXB.

| Compound | Treatment | Concentration inhibiting 50% of bacterial growth ($\mu$M) | Antimicrobial potency[1] (%) |
|---|---|---|---|
| native PMXB | — | 0.05 | 100 |
| native PMXB | 3 d, 37° C., pH 8.5[2] | 0.1 | 100 |
| native PMXB | 6 d, 37° C., pH 8.5[2] | 0.2 | 100 |
| native PMXB | 3 d, 37° C., pH 7.4[3] | 0.055 | 100 |
| native PMXB | 6 d, 37° C., pH 7.4[3] | 0.228 | 100 |
| (Fmoc)$_2$-PMBX | — | 5 | 1 |
| (Fmoc)$_2$-PMBX | 3 d, 37° C., pH 8.5[2] | 0.125 | 80 |
| (Fmoc)$_2$-PMBX | 6 d, 37° C., pH 8.5[2] | 0.2 | 100 |
| (Fmoc)$_2$-PMBX | 3 d, 37° C., pH 7.4[3] | 0.227 | 25 |
| (Fmoc)$_2$-PMBX | 3 d, 37° C., pH 7.4[3] | 0.35 | 64 |

[1]Numbers refer to the potency of PMXB employed as a control throughout the assays.
[2]Incubation was carried out at pH 8.5 with PMXB, or (Fmoc)$_2$-PMXB (100 $\mu$g/ml) in 0.1 M NaHCO$_3$ containing 1% DMSO.
[3]Incubation was carried out at pH 7.4 with PMXB, or (Fmoc)$_2$-PMXB (100 $\mu$g/ml) in 50 mM Hepes-buffer (pH 7.4), containing 1% DMSO.

Analytical HPLC (RP-18; 250×4 mm; Merck) employing linear gradient formed from 70% solution A (0.1% TFA in water) and 30% solution B (0.1% TFA in acetonitrile:water, 75:25), to 100% solution B in 40 minutes (flow rate of 0.8 mL/min), showed one main product eluted at 39 min (retention time of PMXB under these conditions is 13.5 min). The crude solid was applied to preparative HPLC to provide a pure product. Analysis of (Fmoc)$_2$-PMXB by mass spectrum (FAB), gave the expected molecular weight for this compound (M/Z 1647 [M-H]$^+$).

The antibacterial potencies of (Fmoc)$_2$-PMXB and of native PMXB were assayed under various experimental conditions as follows: a dilute suspension of *E. Coli* (0.5 ml per glass test tube) was incubated for 6 hours at 37° C. without or with increased concentrations of (Fmoc)$_2$-PMXB and native PMXB. At the indicated time points aliquots were withdrawn and analyzed for their potencies to arrest growth of *E. coli*, and bacterial growth was then evaluated by measuring turbidity at 700 nm.

As shown in Table VII, (Fmoc)$_2$-PMXB is inactive (~1%) and is largely hydrolyzed back to active PMXB with $t_{1/2}$ values of~3 and ~1 days at pH 8.5 and 7.4, respectively.

Example 10
Preparation of Piperacillin-fluorenylmethyl Ester (Piperacillin-O-Fm)

Piperacillin (4-ethyl-2,3-dioxopiperazinecarbonyl ampicillin) is a broad spectrum semi-synthetic antibiotic related to penicillin, which is not effective when administered orally.

Piperacillin (free carboxyl) was prepared from piperacillin sodium salt (Sigma, USA) by acidic extraction with ethyl acetate. Piperacillin-OFm was synthesized as described for cephalexin-OFm ester in Example 8 above, by reacting 1 equivalent of carboxyl with 2 equivalents, each, of 9-fluorenylmethanol, 4-dimethylaminopyridine and DCC. The crude solid was recrystallized from DCM-ether, yielding a pure product as confirmed by TLC and HPLC procedures.

Example 11
Preparation of Fmoc-propranolol

Propananolol [1-(isopropylamino)-3-(1-naphthyloxy)-2-propanol], a representative member of the beta blockers family, is a β-adrenergic antagonist used as antihypertensive, antianginal and antiarrhythmic. Propranolol binds, but does not activate, the β-adrenergic receptor. Competition for these sites with β-adrenergic antagonists reduces pathological hypertensive states. Patients receive propranolol orally on a daily basis. However, a vast majority of β-adrenergic antagonists are rather hydrophilic in nature, and are not absorbed efficiently while administered orally, e.g. acetylbutolol, athenolol, betaxolol, carteolol, nadolol, and sotalol.

For the preparation of Fmoc-propranolol, a solution of Fmoc-OSu (170 mg, 0.50 indole) in DCM (2.5 ml) was added dropwise over 5 min to a stirred solution of (±)-propranolol hydrochloride (50 mg, 0.17 mmole) and triethylamine (34 mg, 0.34 mmole) in dichloromethane (DCM, 2.5 ml).

After stirring overnight at room temperature, the reaction mixture was extracted with acidified water (pH~2), water and brine, and dried over anhydrous MgSO$_4$. The solution was evaporated to furnish crude solid which was then triturated with hexane to give Fmoc-propranolol. The product was examined by TLC (1-butanol: acetic acid:water, 8:1:1) and HPLC, and proved to be pure (retention times of propranolol and Fmoc-propranolol, under the same conditions, are 16 and 51 min, respectively). Mass spectrum (FAB) gave the correct M/Z: 482.2[M+H]+$^+$.

Figure 7:
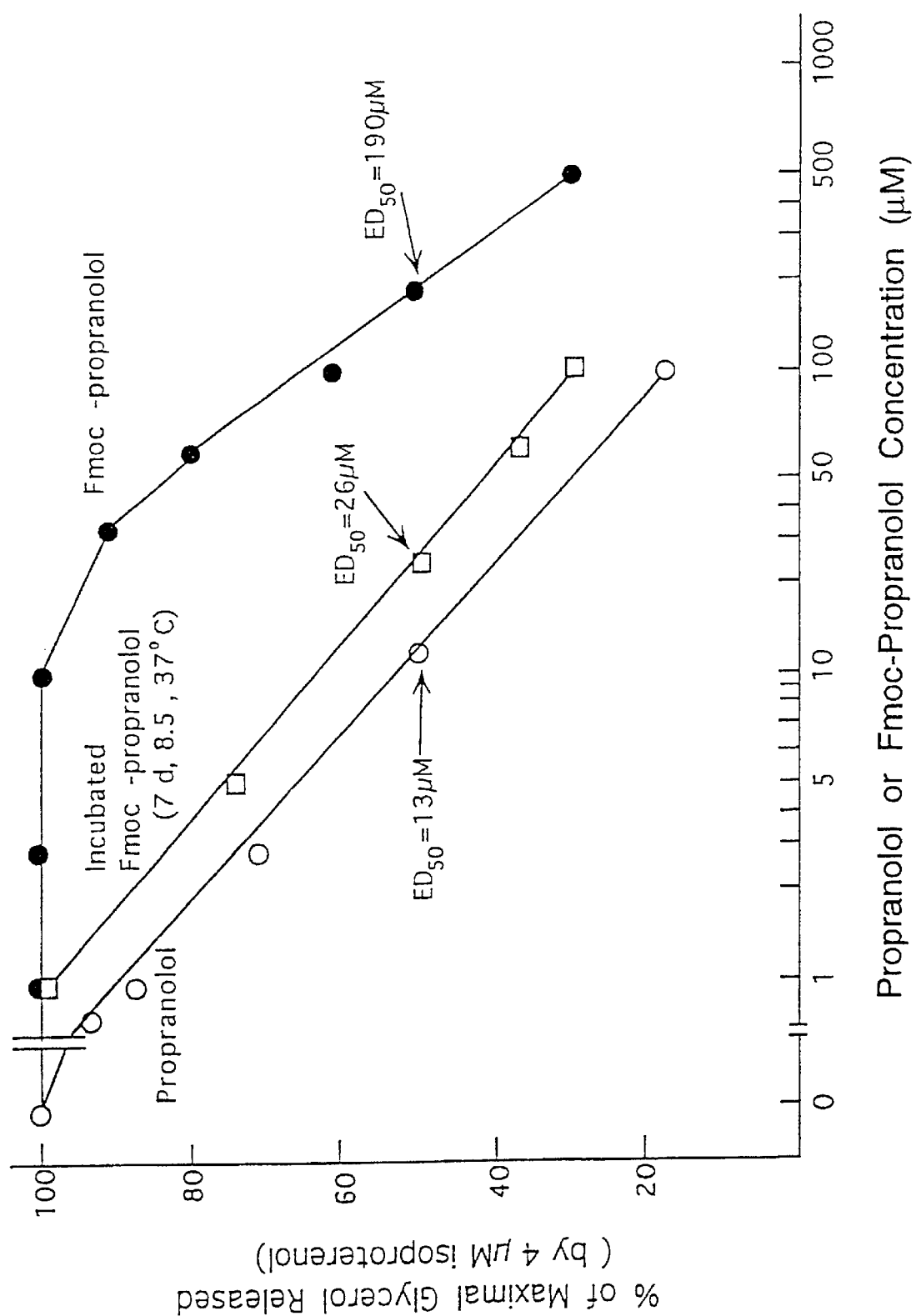
FIG. 7 shows the β-adrenergic antagonistic potency of N-Fmoc-propranolol through the generation of active propranolol upon incubation.

The β-adrenergic potency of Fmoc-propranolol was analyzed. The results are shown in FIG. 7. Freshly prepared rat adipocytes were incubated for 2 hrs at 37° C., with isoproterenol (final concentration 1 μg/ml, 4 μM) and the indicated concentrations of propranolol (circles), Fmoc-propranolol (filled circles) or Fmoc-propranolol that was incubated for 7 days at 37° C., pH 8.5 (squares). The amount of glycerol released to the medium was then determined according to Shechter, 1982. IC$_{50}$ is the amount of propranolol or N-Fmoc-propranolol derivative (in μM) that inhibited isoproterenol-mediated glycerol release, half maximally.

As shown in FIG. 7, Fmoc-propranolol has ~7% of the potency of native propranolol. Incubation of Fmoc-propranolol for 7 days at pH 8.5 (37° C.) generated 50–70% of the native drug β-adrenergic potency. The derivative is substantially hydrophobic, a feature that may assist in gastrointestinal absorption.

REFERENCES

1. Bodanszky, M. and Bednarek, M. (1982) Int. J. Peptide Protein Res. 20, 434–37.
2. Burch, R. M., Weitzberg, M., Blok, N., Muhlhauser, R., Martin, D., Farmer, S. G., Bator, J. M., Connor, J. R., Ko, C., Kuhn, W., MCMillan, B. A., Maureen, R., Shearer, B. G., Tiffany, C. and Wilkins, D. E. (1991) Proc. Natl. Acad. Sci. USA 88,355–359.
3. Campbell, R. K., Campbell, L. K., White, J. R. (1996) Ann. Pharmacother. 30, 1263–71.
4. Gertler, A., Ashkenazi, A. and Madar, Z. (1984) Mol. Cell Endocrinol. 34, 51–57.
5. Kaarsholm, N. C. and Ludvigsen, S. (1995) Receptor 5, 1–8.
6. Meyerovitch, J., Farfel, Z., Sack, J. and Shechter, Y. (1987) J. Biol. Chem. 262, 6658–6662.
7. Meyerovitch, J., Kahn, C. R. and Shechter, Y. (1990) Biochemistry 29,3654–3660.
8. Moody, A. J., Stan, M. A., Stan, M. and Gliemann, J. (1974) Horm. Metab. Res.6, 12–16.
9. Pederson, R. A., Ramanadham, S., Buchan, A. M. J. and MCNeill, J. H. (1989) Diabetes 38, 1390–1395.
10. Rodbell, M. (1964) J. Biol. Chem.239,375–380.
11. Shechter, Y. (1982) Endocrinology 110, 1579–1583
12. Shechter, Y. and Ron, A. (1986) J. Biol. Chem.261, 14945–14950

What is claimed is:

1. A prodrug that slowly hydrolyzes to the original active drug molecule under physiological conditions, said prodrug being of the formula:

$(X)_n$—Y wherein

Y consists of an antidiabetic drug bearing at least one functional group selected from free amino, carboxyl, hydroxyl and/or mercapto, and X is a radical selected from the group of radicals consisting of the formulas (i) to (iv):

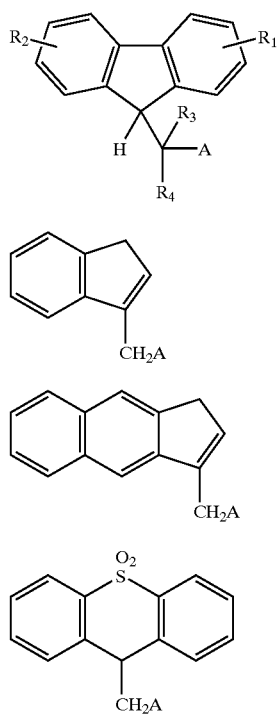

wherein $R_1$ and $R_2$, the same or different, are each hydrogen, alkyl, alkoxy, alkoxyalkyl, aryl, alkaryl, aralkyl, halogen, nitro, sulfo, amino, ammonium, carboxyl, $PO_3H_2$, or $OPO_3H_2$; $R_3$ and $R_4$, the same or different, are each hydrogen, alkyl or aryl; and A is a covalent bond when the radical is linked to a carboxyl or mercapto group of the drug Y, or A is OCO— when the radical is linked to an amino or hydroxyl group of Y, n is an integer of at least one, and pharmaceutically acceptable salts thereof, wherein said radical (i) in which each of $R_1$, $R_2$, $R_3$ and $R_4$ is a hydrogen atom and A is OCO— (9-fluorenylmethoxycarbonyl) is hereafter referred to as Fmoc, said radical (i) in which each of $R_1$, $R_2$, $R_3$ and $R_4$ is a hydrogen atom and A is a covalent bond (9-fluorenylmethyl) is hereafter referred to as Fm, and said radical (i) in which $R_1$ is 2-sulfo, each of $R_2$, $R_3$ and $R_4$ is a hydrogen atom and A is OCO— (2-sulfo-9-fluorenylmethoxycarbonyl) is hereafter referred to as Sulfmoc.

2. A prodrug according to claim 1, wherein X is a radical of formula (i).

3. A prodrug according to claim 1 in which Y is substituted by at least one radical X consisting of a radical (i) wherein $R_1$ is hydrogen or sulfo and each of $R_2$, $R_3$ and $R_4$ is a hydrogen atom.

4. A prodrug according to claim 3, in which Y is insulin in which free amino and/or carboxyl groups, and optionally free hydroxyl groups, of the insulin, are linked to at least one said radical (i).

5. A prodrug according to claim 4, wherein one or more amino groups are linked to an Fmoc radical.

6. A prodrug according to claim 4, wherein one or more carboxyl groups are linked to an Fm radical.

7. A prodrug according to claim 4, wherein one or more amino groups are linked to an Fmoc radical and one or more carboxyl groups are linked to an Fm radical.

8. A prodrug according to claim 4, wherein one or more carboxyl groups are linked to an Fm radical and one or more hydroxyl groups are linked to an Fmoc radical.

9. A prodrug according to claim 4, wherein one or more amino and hydroxyl groups are linked to an Fmoc radical and one or more carboxyl groups are linked to an Fm radical.

10. A prodrug according to claim 4, wherein Y is human insulin and wherein the prodrug has 1 to 3 Fmoc substituents at the free amino groups at positions $Gly^{A1}$, $Phe^{B1}$ or $Lys^{B29}$, wherein A and B are the chains of the insulin molecule, selected from the group of insulin derivatives consisting of $Gly^{A1}$-N-(Fmoc)-insulin; $Phe^{B1}$-N-(Fmoc)-insulin; $Lys^{B29}$-N-(Fmoc)-insulin; $Gly^{A1}$, $Phe^{B1}$-N-(Fmoc)$_2$-insulin; $Gly^{A1}$, $Lys^{B29}$-N-(Fmoc)$_2$-insulin; $Phe^{B1}$, $Lys^{B29}$-N-(Fmoc)$_2$-insulin; and $Gly^{A1}$, $Phe^{B1}$, $Lys^{B29}$-N-(Fmoc)$_3$-insulin.

11. A prodrug according to claim 4, wherein Y is human insulin and wherein the prodrug has 1 to 3 Sulfmoc substituents at the free amino groups at positions $Gly^{A1}$, $Phe^{B1}$, or $Lys^{B29}$, wherein A and B are the chains of the insulin molecule, selected from the group of insulin derivatives consisting of $Gly^{A1}$-N-(Sulfmoc)-insulin; $Phe^{B1}$-N-(Sulfmoc)-insulin; $Lys^{B29}$-N-(Sulfmoc)-insulin; $Gly^{A1}$, $Phe^{B1}$-N-(Sulfmoc)$_2$-insulin; $Gly^{A1}$, $Lys^{29}$-N-(Sulfmoc)$_2$-insulin; $Phe^{B1}$, $Lys^{B29}$-N-(Sulfmoc)$_2$-insulin; and $Gly^{A1}$, $Phe^{B1}$, $Lys^{B29}$-N-(Sulfmoc)$_3$-insulin.

12. A prodrug according to claim 4, wherein the insulin is human, bovine or porcine insulin.

13. A pharmaceutical composition comprising a prodrug according to claim 4 or a pharmaceutically acceptable salt thereof, and a pharmaceutically acceptable carrier.

14. A pharmaceutical composition according to claim 13, comprising human N,N',N"-(Fmoc)$_3$-insulin and/or human N,N'-(Fmoc)$_2$ insulin.

15. A pharmaceutical composition comprising a prodrug according to claim 1 or a pharmaceutically acceptable salt thereof, and a pharmaceutically acceptable carrier.

16. A pharmaceutical composition according to claim 15, wherein said pharmaceutically acceptable carrier is chosen so as to be suitable for subcutaneous injection, transdermal or oral administration.

17. A method for the treatment of diabetes, comprising administering to a diabetic patient one prodrug, or more than one prodrug, according to claim 4 for a time and under conditions effective to reduce the concentration of glucose in the blood of the patient.

18. A method according to claim 17, wherein said prodrug is N,N'-(Fmoc)$_2$-insulin or N,N',N"-(Fmoc)$_3$-insulin, and said one or more prodrug(s) is or are administered to the patient at 5–8 day intervals.

19. A method according to claim 17, wherein said one or more N-(Fmoc)-insulin(s) is or are administered by subcutaneous injection.

20. A method according to claim 17, wherein said method further comprises administering insulin at least once per day to said patient.

21. A compound of the formula:

wherein

Y consists of an antidiabetic drug bearing at least one functional group selected from free amino, carboxyl, hydroxyl and/or mercapto, and X is a radical selected from the group of radicals consisting of the formulas (i) to (iv):

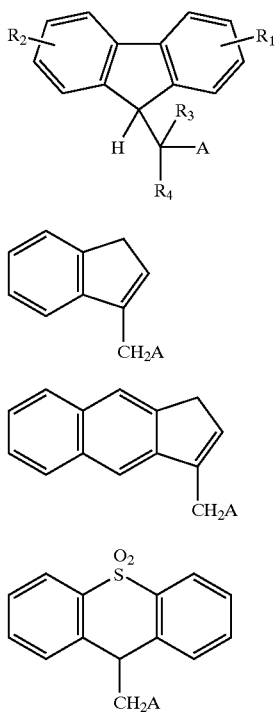

wherein $R_1$ and $R_2$, the same or different, are each hydrogen, alkyl, alkoxy, alkoxyalkyl, aryl, alkaryl, aralkyl, halogen, nitro, sulfo, amino, ammonium, carboxyl, PO$_3$H$_2$, or OPO$_3$H$_2$; $R_3$ and $R_4$, the same or different, are each hydrogen, alkyl or aryl; and A is a covalent bond when the radical is linked to a carboxyl or mercapto group of the drug Y, or A is OCO— when the radical is linked to an amino or hydroxyl group of Y, n is an integer of at least one, and pharmaceutically acceptable salts thereof, wherein said radical (i) in which each of $R_1$, $R_2$, $R_3$ and $R_4$ is a hydrogen atom and A is OCO— (9-fluorenylmethyoxycarbonyl) is hereafter referred to as Fmoc, said radical (i) in which each of $R_1$, $R_2$, $R_3$ and $R_4$ is a hydrogen atom and A is a covalent bond (9-fluorenylmethyl) is hereafter referred to as Fm, and said radical (i) in which $R_1$ is 2-sulfo, each of $R_2$, $R_3$ and $R_4$ is a hydrogen atom and A is OCO— (2-sulfo-9-fluorenylmethoxycarbonyl) is hereafter referred to as Sulfmoc.

22. A compound according to claim 21 in which Y is substituted by at least one radical X consisting of a radical (i) wherein $R_1$ is hydrogen or sulfo and each of $R_2$, $R_3$ and $R_4$ is a hydrogen atom.

23. A compound according to claim 22, in which Y is insulin in which free amino and/or carboxyl groups, and optionally free hydroxyl groups, of the insulin, are linked to at least one said radical (i).

24. A compound according to claim 23, wherein one or more amino groups are linked to an Fmoc radical.

25. A compound according to claim 23, wherein one or more carboxyl groups are linked to an Fm radical.

26. A compound according to claim 23, wherein one or more amino groups are linked to an Fmoc radical and one or more carboxyl groups are linked to an Fm radical.

27. A compound according to claim 23, wherein one or more carboxyl groups are linked to an Fm radical and one or more hydroxyl groups are linked to an Fmoc radical.

28. A compound according to claim 23, wherein one or more amino and hydroxyl groups are linked to an Fmoc radical and one or more carboxyl groups are linked to an Fm radical.

29. A compound according to claim 23, wherein Y is human insulin and wherein the compound has 1 to 3 Sulfmoc substituents at the free amino groups at positions Gly$^{A1}$, Phe$^{B1}$ or Lys$^{B29}$, wherein A and B are the chains of the insulin molecule, selected from the group of insulin derivatives consisting of Gly$^{A1}$-N-(Sulfmoc)-insulin; Phe$^{B1}$-N-(Sulfmoc)-insulin; Lys$^{B29}$-N-(Sulfmoc)-insulin; Gly$^{A1}$, Phe$^{B1}$-N-(Sulfmoc)$_2$-insulin; Gly$^{A1}$, Lys$^{B29}$-N-(Sulfmoc)$_2$-insulin; Phe$^{B1}$, Lys$^{B29}$-N-(Sulfmoc)$_2$-insulin; and Gly$^{A1}$, Phe$^{B1}$, Lys$^{B29}$-N-(Sulfmoc)$_3$-insulin.

30. A compound according to claim 23, wherein Y is human insulin and wherein the compound has 1 to 3 Fmoc substituents at the free amino groups at positions Gly$^{A1}$, Phe$^{B1}$ or Lys$^{B29}$, wherein A and B are the chains of the insulin molecule, selected from the group of insulin derivatives consisting of Gly$^{A1}$-N-(Fmoc)-insulin; Phe$^{B1}$-N-(Fmoc)-insulin; Lys$^{B29}$-N-(Fmoc)-insulin; Gly$^{A1}$, Phe$^{B1}$-N-(Fmoc)$_2$-insulin; Gly$^{A1}$, Lys$^{B29}$-N-(Fmoc)$_2$-insulin; Phe$^{B1}$, Lys$^{B29}$-N-(Fmoc)$_2$-insulin; and Gly$^{A1}$, Phe$^{B1}$, Lys$^{B29}$-N-(Fmoc)-insulin.

31. A compound according to claim 23, wherein the insulin is human, bovine or porcine insulin.

32. A compound of the formula:

wherein

Y is a biologically active drug bearing at least one functional group selected from free amino, carboxyl, hydroxyl and/or mercapto selected from the group consisting of human growth hormone, bovine growth hormone, cephalexin, polymyxin B, piperacillin and propanolol, and X is a radical selected from the group of radicals consisting of the formulas (i) to (iv):

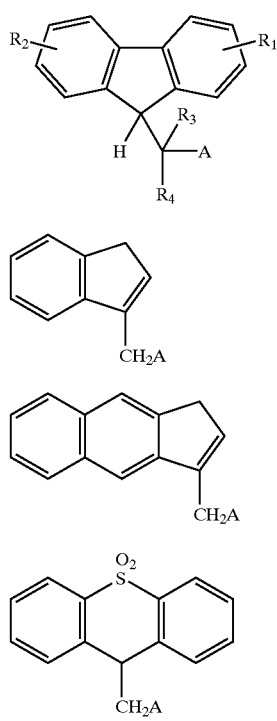

wherein $R_1$ and $R_2$, the same or different, are each hydrogen, alkyl, alkoxy, alkoxyalkyl, aryl, alkaryl, aralkyl, halogen, nitro, sulfo, amino, ammonium, carboxyl, $PO_3H_2$, or $OPO_3H_2$; $R_3$ and $R_4$, the same or different, are each hydrogen, alkyl or aryl; and A is a covalent bond when the radical is linked to a carboxyl or mercapto group of the drug Y, or A is OCO— when the radical is linked to an amino or hydroxyl group of Y, n is an integer of at least one, and pharmaceutically acceptable salts thereof, wherein said radical (i) in which each of $R_1$, $R_2$, $R_3$ and $R_4$ is a hydrogen atom and A is OCO— (9-fluorenylmethyoxycarbonyl) is hereafter referred to as Fmoc, said radical (i) in which each of $R_1$, $R_2$, $R_3$ and $R_4$ is a hydrogen atom and A is a covalent bond (9-fluorenylmethyl) is hereafter referred to as Fm, and said radical (i) in which $R_1$ is 2-sulfo, each of $R_2$, $R_3$ and $R_4$ is a hydrogen atom and A is OCO— (2-sulfo-9-fluorenylmethoxycarbonyl) is hereafter referred to as Sulfmoc.

33. A compound according to claim 32, wherein X is a radical of formula (i).

34. A compound according to claim 32, wherein X is radical (i) and Y is a human or bovine growth hormone.

35. A compound according to claim 32, wherein X is Fmoc or Fm and Y is cephalexin.

36. A compound according to claim 32, wherein X is di-Fmoc and Y is polymyxin B.

37. A compound according to claim 32, wherein X is Fm and Y is piperacillin.

38. A compound according to claim 32, wherein X is radical (i) and Y is propranolol.

39. A pharmaceutical composition comprising a compound according to claim 32, or a pharmaceutically acceptable salt thereof, and a pharmaceutically acceptable carrier.

* * * * *